United States Patent [19]

Matula et al.

[11] Patent Number: 5,554,101
[45] Date of Patent: Sep. 10, 1996

[54] SURGICAL RETRACTOR

[75] Inventors: Paul A. Matula, Brookfield, Conn.; Stanley H. Remiszewski, Bolton, Mass.

[73] Assignee: United States Surgical Corporation, Norwalk, Conn.

[21] Appl. No.: 361,933

[22] Filed: Dec. 22, 1994

Related U.S. Application Data

[63] Continuation of Ser. No. 874,743, Apr. 27, 1992, Pat. No. 5,381,788, which is a continuation-in-part of Ser. No. 740,443, Aug. 5, 1991, Pat. No. 5,199,419.

[51] Int. Cl.$^6$ .................................................. A61B 17/02
[52] U.S. Cl. ........................ 600/214; 600/204; 600/219; 606/191
[58] Field of Search .................................... 600/201, 204, 600/210, 214, 219, 224, 225; 606/191, 205

[56] References Cited

U.S. PATENT DOCUMENTS

| | | |
|---|---|---|
| 972,983 | 10/1910 | Arthur . |
| 1,244,751 | 10/1917 | McCleary . |
| 1,328,624 | 1/1920 | Graham . |
| 2,202,748 | 5/1940 | Solo . |
| 2,816,552 | 12/1957 | Hoffmann . |
| 3,313,294 | 4/1967 | Uddenberg . |
| 3,314,431 | 4/1967 | Smith, Jr. . |
| 3,467,079 | 9/1969 | James . |
| 4,130,113 | 12/1978 | Graham . |
| 4,190,042 | 2/1980 | Sinnreich . |
| 4,226,228 | 10/1980 | Shin et al. . |
| 4,459,978 | 7/1984 | Kotsanis . |
| 4,559,944 | 12/1985 | Jaeger . |
| 4,580,568 | 4/1986 | Gianturco . |
| 4,585,000 | 4/1986 | Hershenson . |
| 4,654,028 | 3/1987 | Suma . |
| 4,655,219 | 4/1987 | Petruzzi . |
| 4,656,999 | 4/1987 | Storz . |
| 4,688,555 | 8/1987 | Wardle . |
| 4,765,311 | 8/1988 | Kulik et al. . |
| 4,773,400 | 9/1988 | Borodulin et al. . |
| 4,872,456 | 10/1989 | Hasson . |
| 4,909,789 | 3/1990 | Taguchi et al. . |
| 4,945,920 | 8/1990 | Clossick . |
| 4,990,156 | 2/1991 | Lefebvre . |
| 4,994,079 | 2/1991 | Genese et al. . |
| 5,034,001 | 7/1991 | Garrison et al. . |
| 5,035,248 | 7/1991 | Zinnecker . |

(List continued on next page.)

FOREIGN PATENT DOCUMENTS

| | | |
|---|---|---|
| 0380874 | 8/1990 | European Pat. Off. . |
| 325846 | 9/1902 | France . |
| 9106506 | 5/1991 | Germany . |
| 736949 | 5/1980 | U.S.S.R. . |
| 990220 | 1/1983 | U.S.S.R. . |
| 1360708 | 12/1987 | U.S.S.R. . |
| 9102493 | 3/1991 | WIPO . |

OTHER PUBLICATIONS

J. Sklar Surgical Instrument brochure.
"Levy Articulating Retractor", *Surgical Products*, p. 33, Jun. 1992 edition.
"Jarit Instrument Update", Jamner Surgical Instruments, Inc., Oct. 1991.
"Nanticoke™ Advanced Laparoscopic/Thoracoscopic Instruments For The Next Generation of Endoscopic Surgery", Cabot Medical Corporation, Jan. 1992.
"Advanced Laparoscopy", Snowden–Pencer, Apr. 1992.
"Manual Instruments", Cooper Endoscopy, Oct. 1992.

*Primary Examiner*—Joe Cheng
*Assistant Examiner*—Kelly McGlashen

[57] ABSTRACT

A surgical retractor is provided including a handle portion, a tubular portion extending from the handle portion, and a collapsible retractor assembly connected to a distal end of the tubular portion. The handle portion includes an actuating structure for manipulating the collapsible retractor assembly through the tubular portion. The retractor assembly includes a plurality of retractor blades, a camming assembly connected to the retractor blades and structure for connecting the retractor blades to the actuating structure.

11 Claims, 19 Drawing Sheets

U.S. PATENT DOCUMENTS

| | | |
|---|---|---|
| 5,098,440 | 3/1992 | Hillstead . |
| 5,113,846 | 5/1992 | Hiltebrandt et al. . |
| 5,152,279 | 10/1992 | Wilk . |
| 5,176,700 | 1/1993 | Brown et al. . |
| 5,178,133 | 1/1993 | Pena . |
| 5,195,505 | 3/1993 | Josefsen . |
| 5,195,506 | 3/1993 | Hulfish . |
| 5,245,987 | 9/1993 | Redmond et al. . |

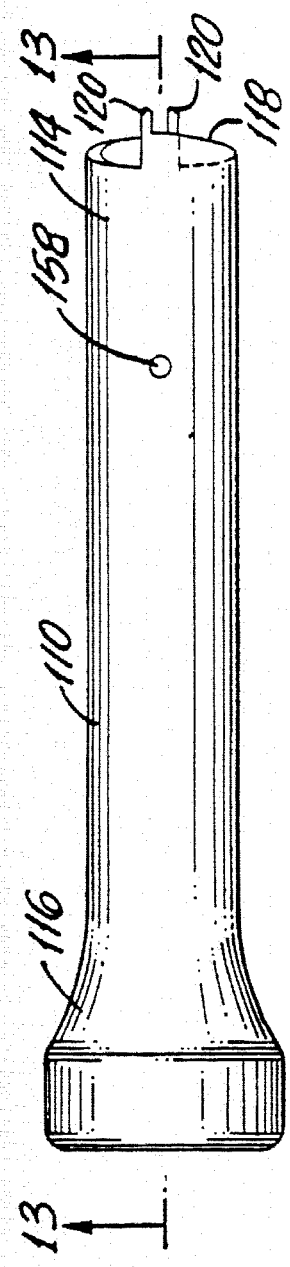
FIG. 12
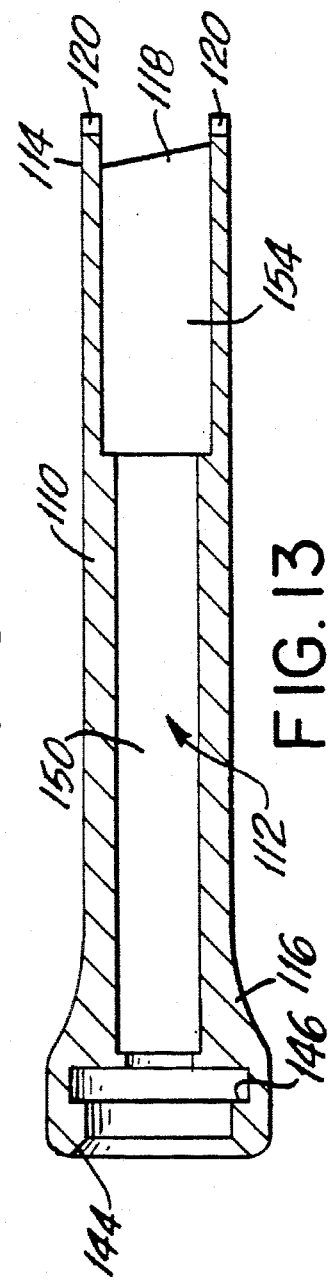
FIG. 13
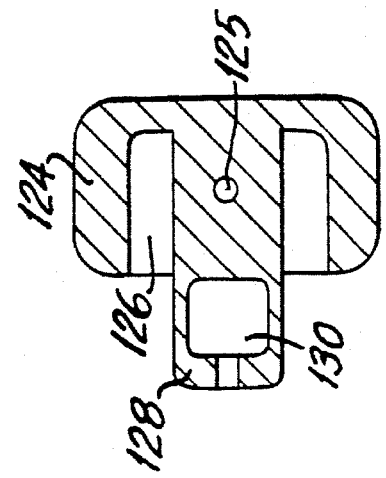
FIG. 15
FIG. 14

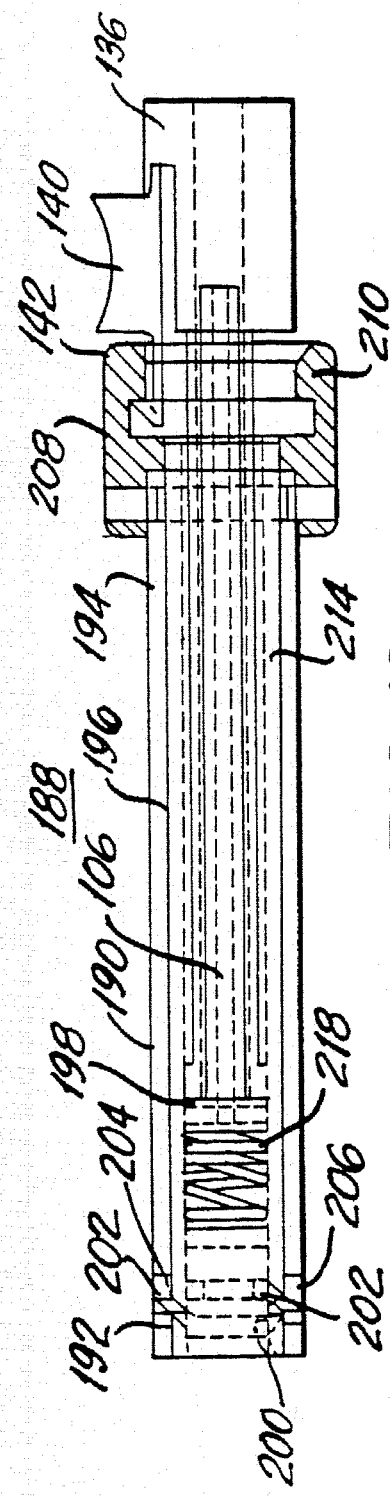
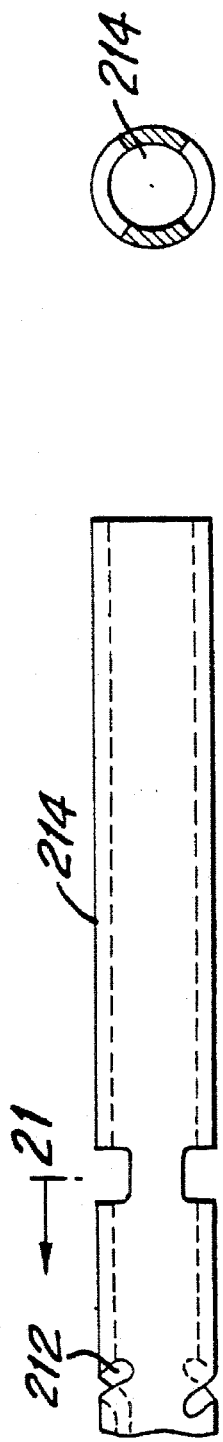
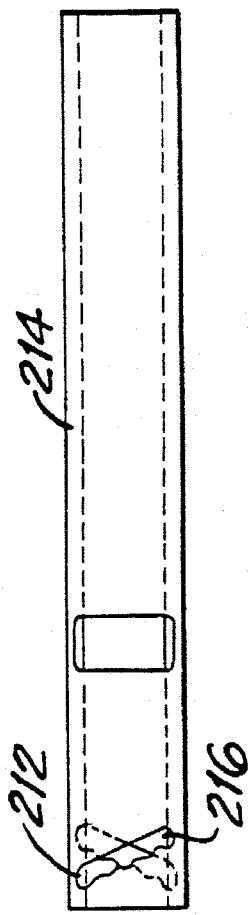
FIG. 19
FIG. 20
FIG. 21
FIG. 22

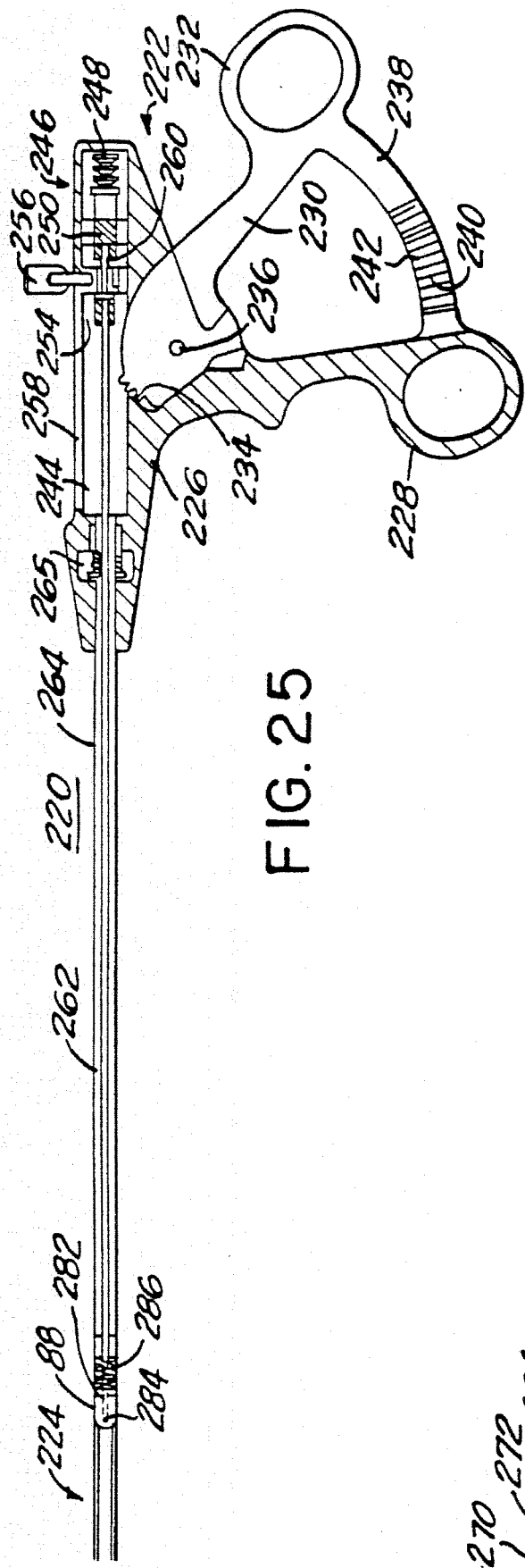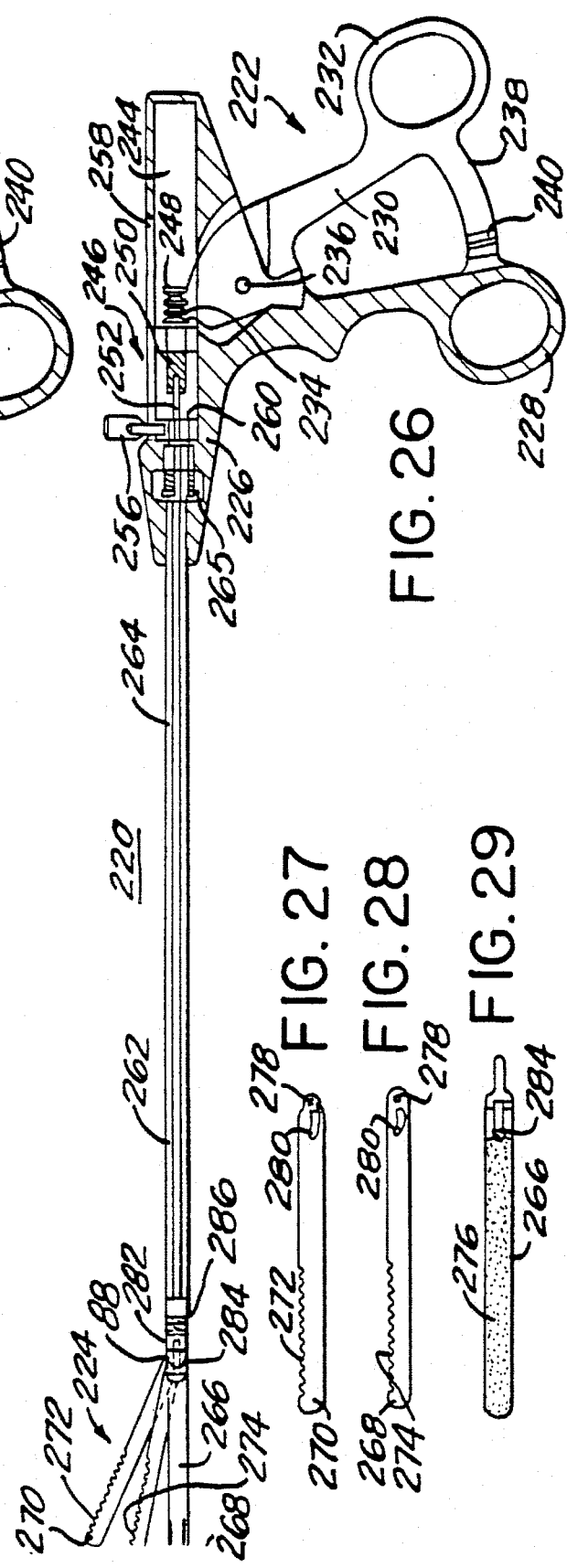

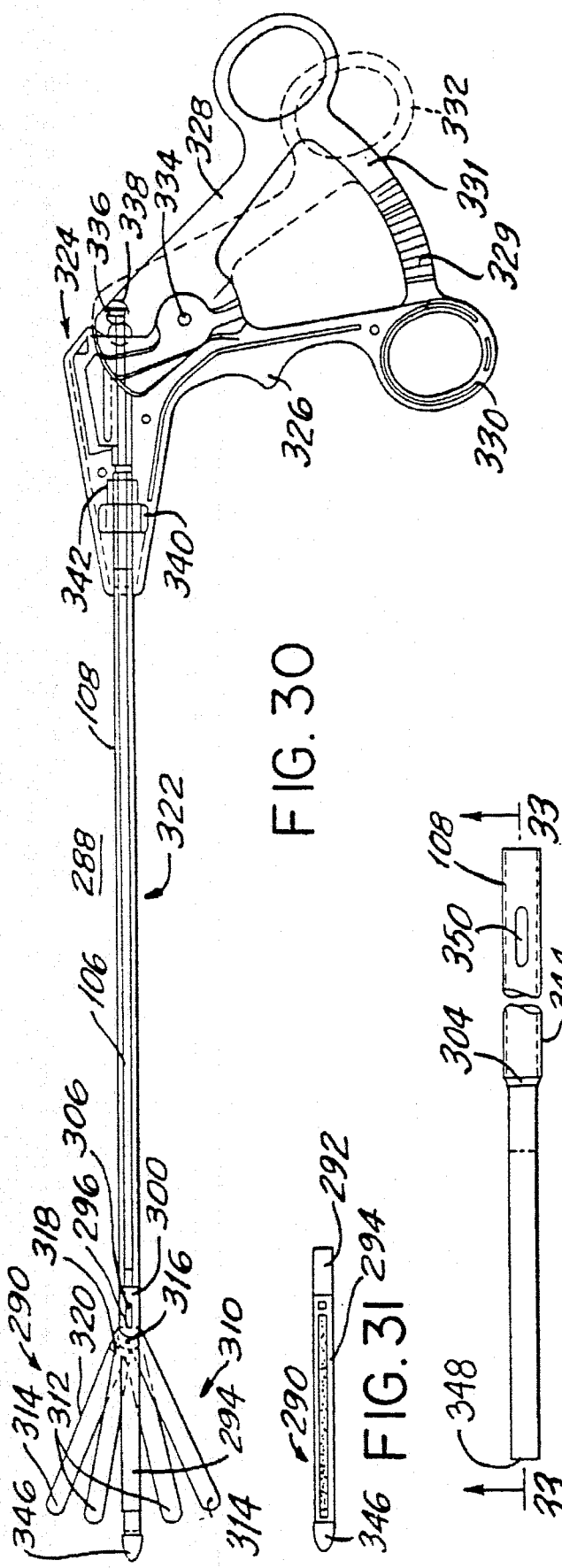

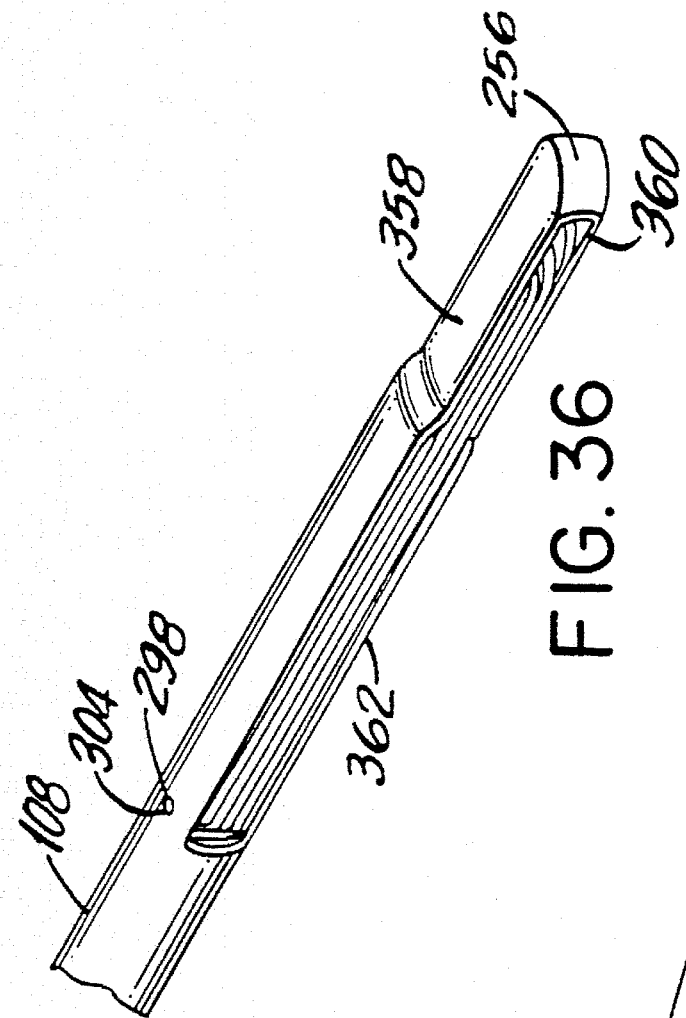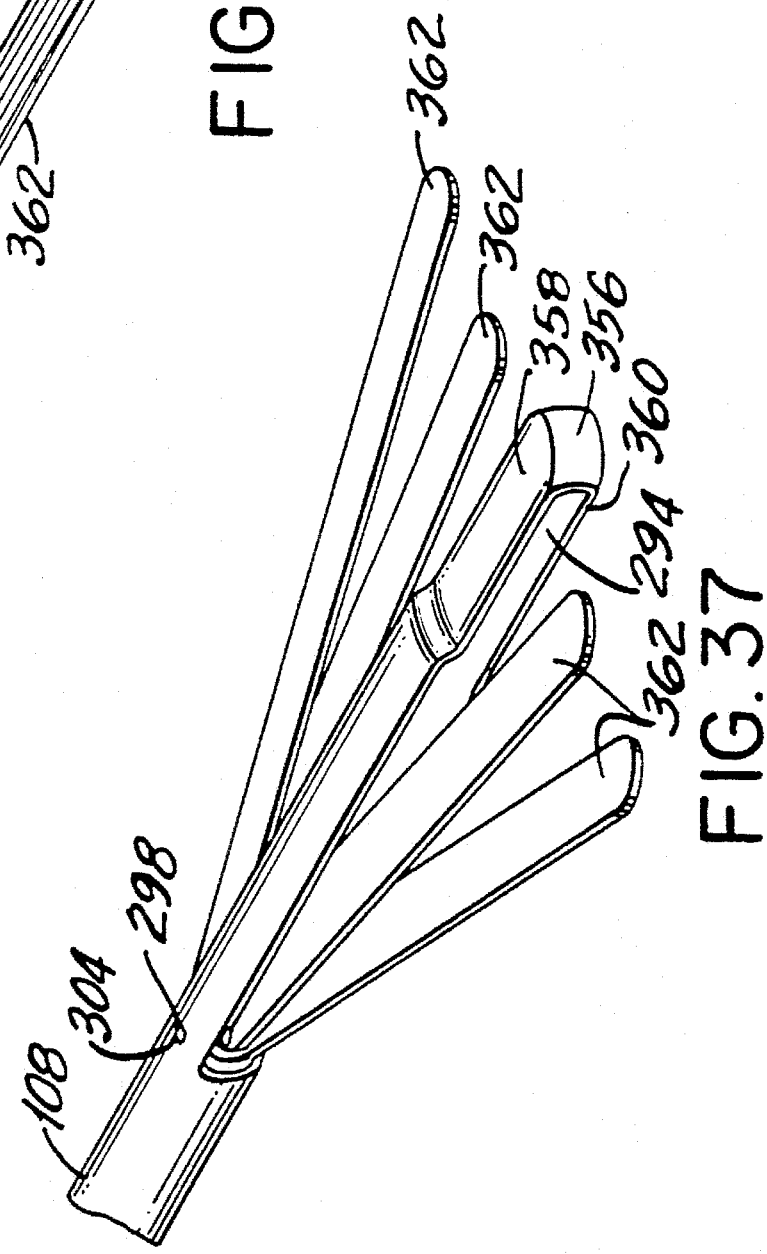

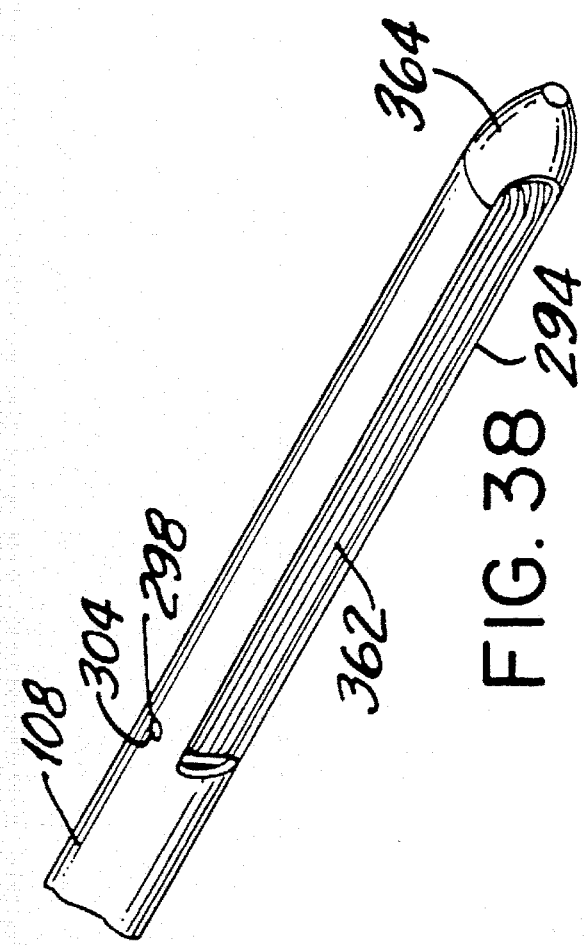
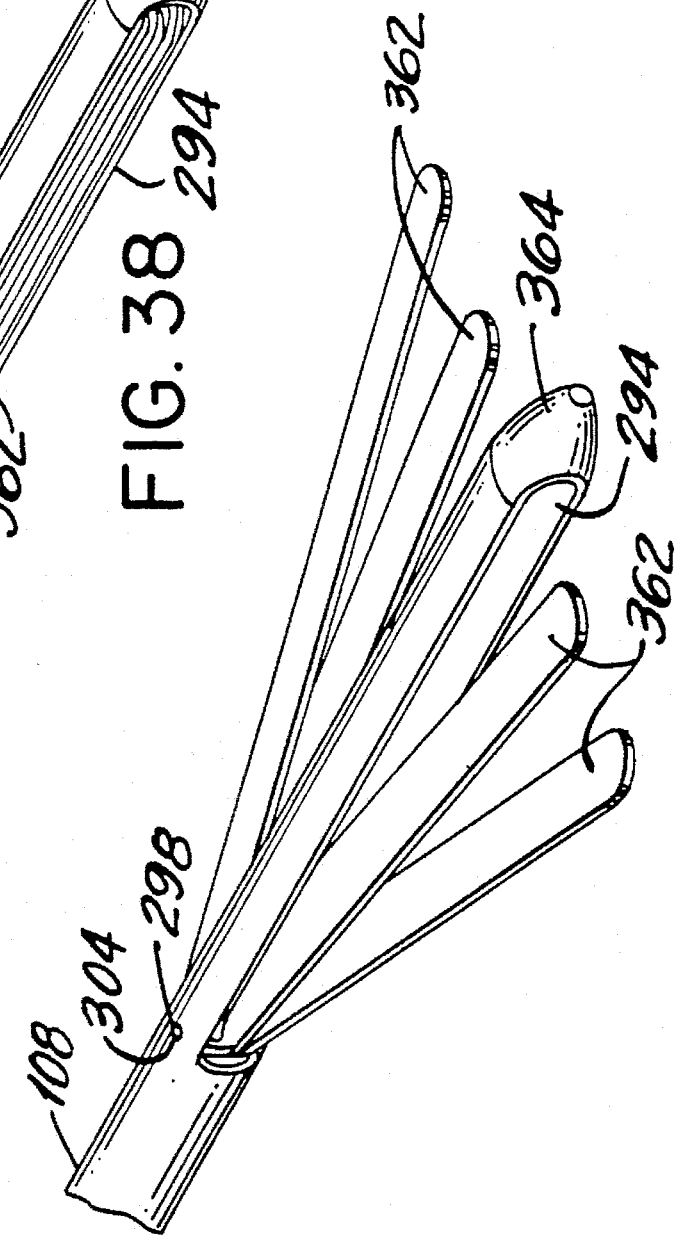

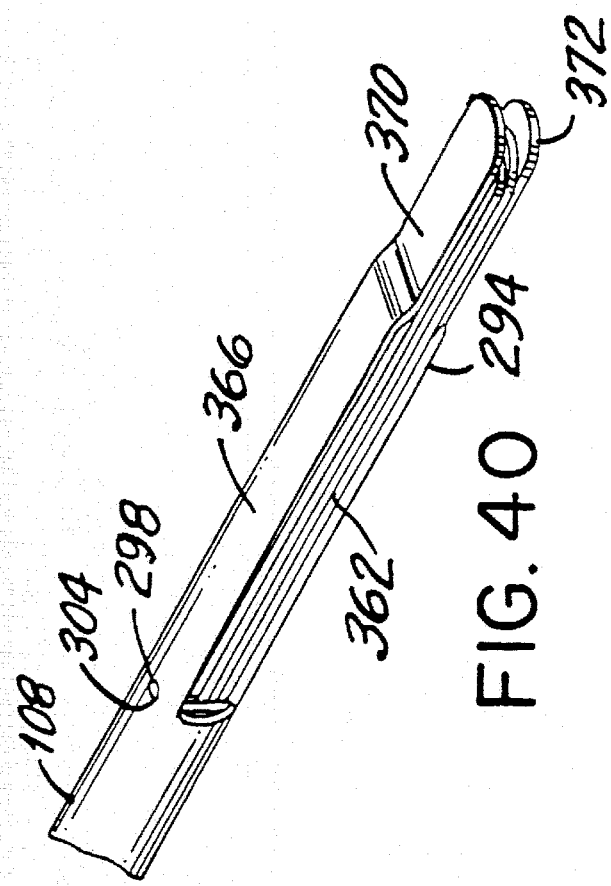
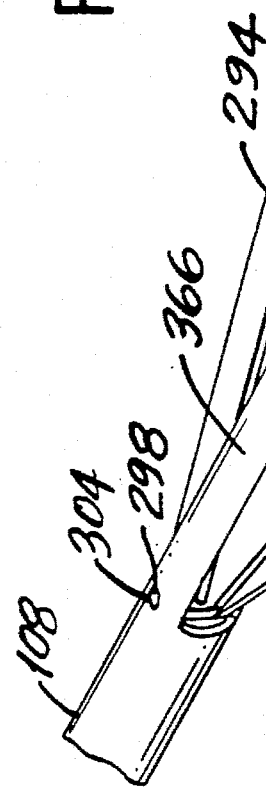

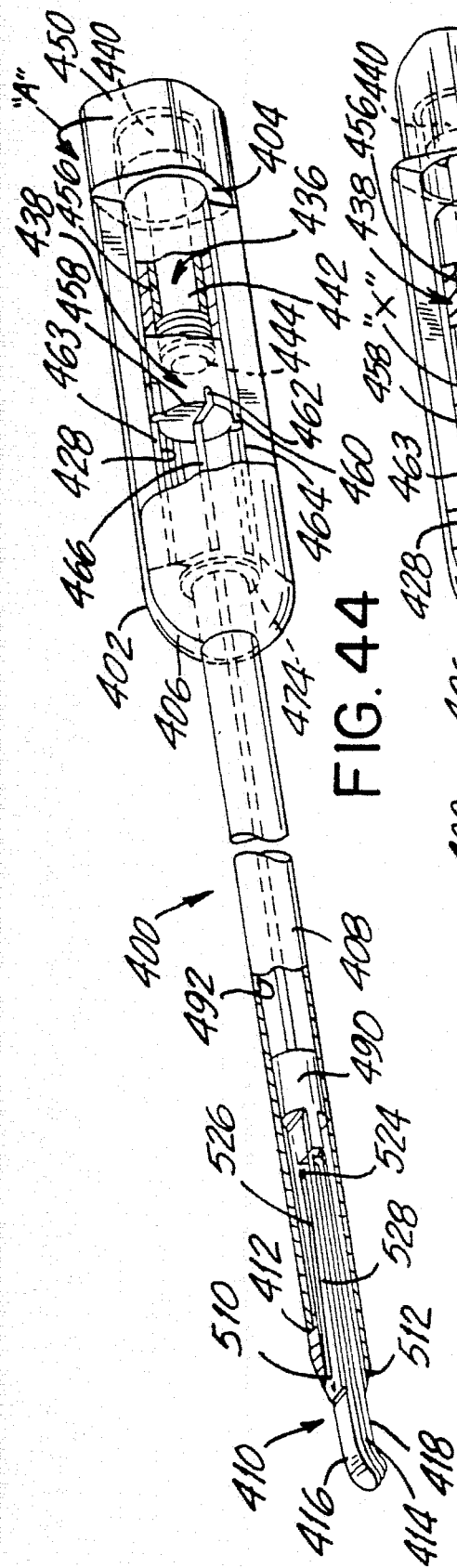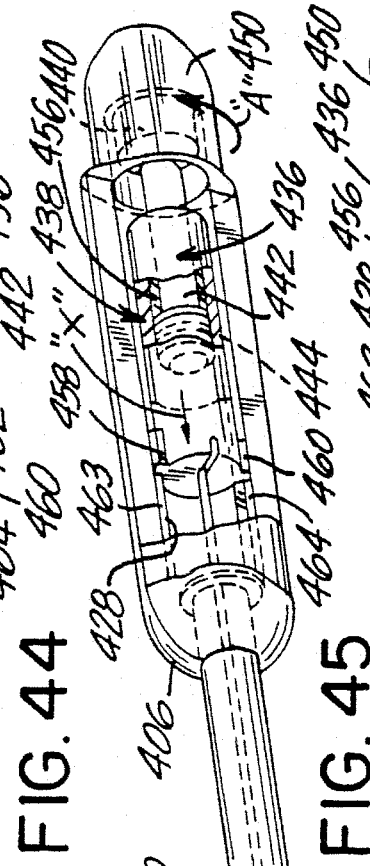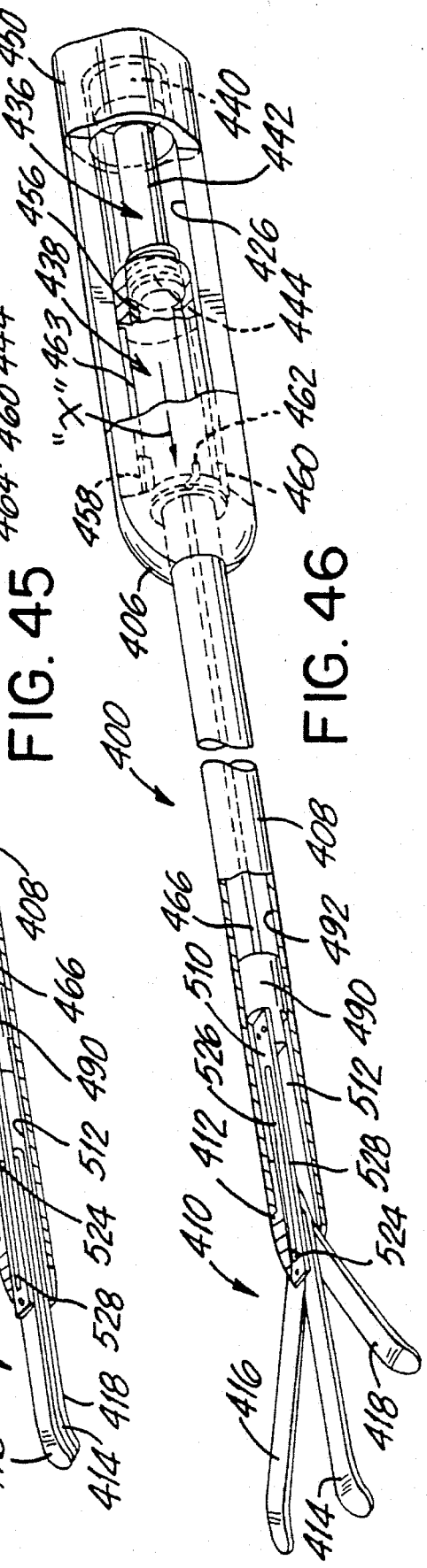

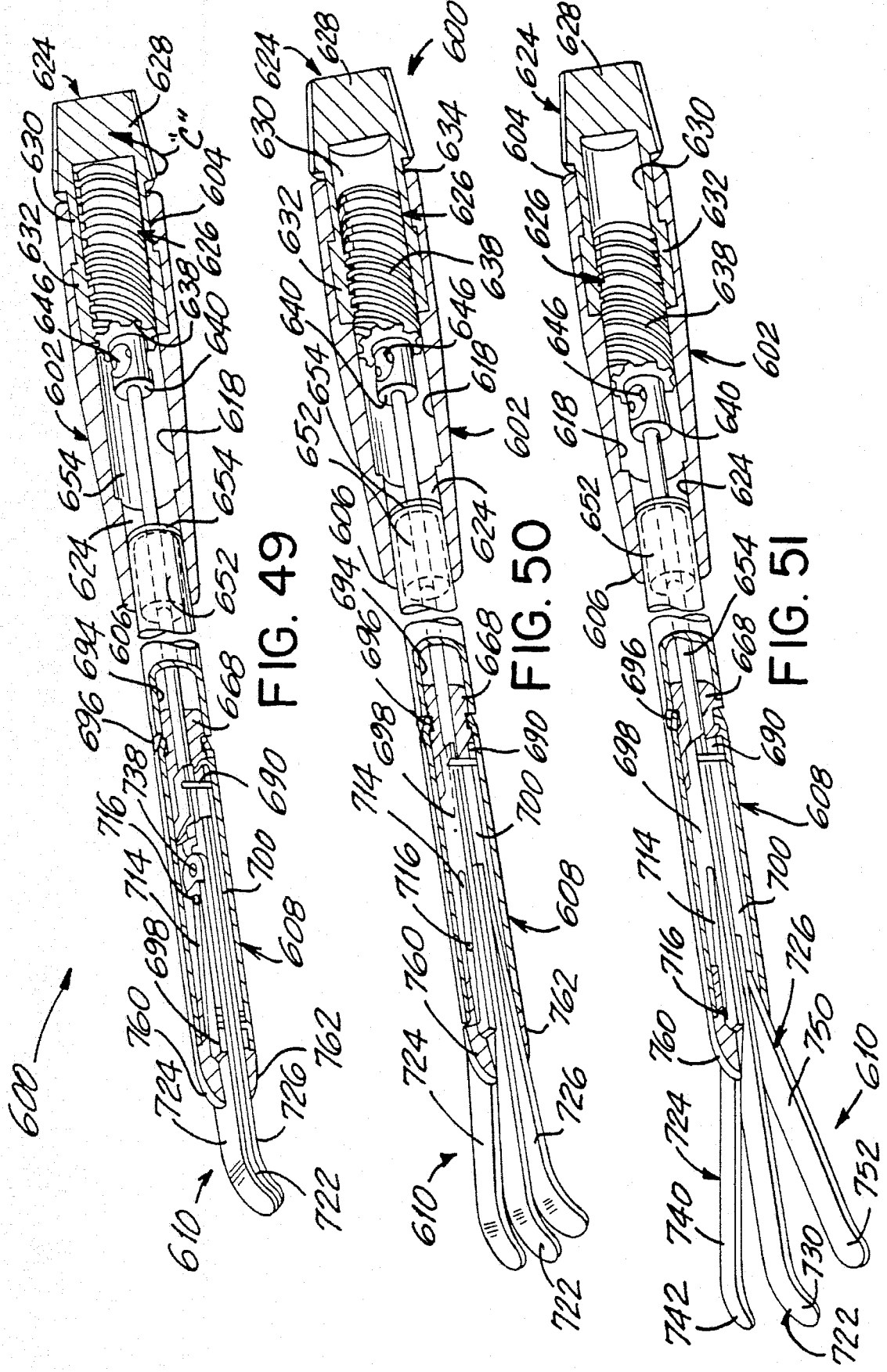

SURGICAL RETRACTOR

CROSS-REFERENCE TO RELATED APPLICATIONS

This application is a continuation of application Ser. No. 07/874,743, filed Apr. 27, 1992, now U.S. Pat. No. 5,381,788, which is a continuation-in-part of application Ser. No. 07/740,443, filed Aug. 5, 1991, now U.S. Pat. No. 5,199,419.

BACKGROUND OF THE INVENTION

1. Field of the Invention

This invention relates generally to surgical instrumentation and, more particularly, to a surgical retractor having deployable blades for use with endoscopic or laparoscopic devices in performing examinations or surgical procedures within body cavities.

2. Description of Related Art

Most endoscopic or laparoscopic procedures are characterized by the provision of an elongated cannula structure having a relatively thin diameter with a proximal and distal end. The distal end is passed through the surrounding tissue into the body cavity wherein the surgical procedure or examination is to be effected, thus providing a conduit for the insertion of surgical instrumentation. A plurality of cannula structures may be used to allow operation of a variety of instruments simultaneously during a given procedure.

In conventional surgical procedures the function of holding tissue and organs in a given location to facilitate access and viewing is typically accomplished by a retractor. This instrumentation is ordinarily in the form of a broad paddle structure or multiple fingers attached to a handle. See, for example, U.S. Pat. No. 3,467,079 (James). This structure, however, is not usable in endoscopic procedures because the retractor is too large to be insertable through the cannula structure into the operative body cavity.

Collapsible intralumen expanders or retractors have taken the form of radial fingers which are activatable to extend relative to each other upon entering the body cavity. See, for example, U.S. Pat. Nos. 4,654,028 (Suma), 4,459,978 (Kotsanis). Dilators of this type are also known. See, for example, U.S. Pat. Nos. 1,328,624 (Graham) and 972,983 (Arthur). In each case, once the retractive or dilatory function is completed, the fingers are compressed and withdrawn. Another collapsible retractor structure includes a pair of collapsible fingers joined by a web of resilient material which, upon insertion into the cannula structure, can expand to form a retractive structure. See, for example, U.S. Pat. No. 4,190,042 (Sinnreich).

Greatly improved retractor structure has been developed and is described in commonly assigned co-pending patent application Ser. No. 07/634,482 filed Dec. 27, 1990. That structure shows a plurality of interleaved retractor blades mounted in a tubular housing. The blades are movable between a closed position and an open position to facilitate ease of insertion and deployment through a cannula. Other surgical apparatus having deployable interleaved retractor blades have been described in Soviet references. See, for example, SU 736-949 (MOME) which describes an instrument having an elongated housing with a plurality of blades operative at one end by means of a manipulator at the opposed end, and SU 1360-708-A (MEDI) which describes an instrument having a plurality of interleaved blades which cannot be manipulated at a distance and thus is unsuited for performing endoscopic or laparoscopic procedures.

SUMMARY OF THE INVENTION

It is an object of the present invention to provide a surgical retractor which overcomes the drawbacks and deficiencies associated with prior art retractors.

Another object of the present invention is to provide a surgical retractor adapted for use in endoscopic and laparoscopic procedures.

A further object of the present invention is to provide a surgical retractor which is easily deployable within a body cavity to provide a retractive function therein.

The present invention provides a novel surgical retractor which has advantageous specific applications in endoscopic and laparoscopic surgical procedures and examinations. The surgical retractor includes a handle assembly, a housing means and a collapsible retractor assembly connected to a distal end of the housing means.

The handle assembly includes a handle in cooperation with an actuating structure for manipulating the collapsible retractor assembly through the housing means in response to relative motion between the actuating structure and the handle. The handle assembly may be configured in a variety of forms including palm grips, pistol grips, axial grips, ring grips, etc.

The housing means, in its most basic embodiment, comprises an elongated tubular structure having an inner tube axially disposed within an outer tube. The outer tube is typically fixed in the stationary handle with the inner tube passing through the outer tube and connected to the actuating structure. The inverse of this configuration, i.e., the inner tube fixed to the stationary handle with the outer tube connected to the actuating structure, is equally useful. Where independent rotation of the tubular housing is desired, the outer tube or inner tube may be rotatably attached to the stationary handle.

A retractor assembly is attached to the distal end of the housing means and includes a reciprocal yoke assembly interconnected with a plurality of collapsible interleaved retractor blades. One element of the yoke assembly is usually maintained stationary while the other is allowed to reciprocate axially to deploy the interleaved retractor blades into a fan configuration.

In alternate embodiments an enclosure tube is provided surrounding the inner and outer tubes. In order to deploy the interleaved retractor blades, the blades are first moved out of the distal end of the enclosure tube.

In preferred embodiments of the subject invention the retractor assembly may include a plurality of retractor blades each having an elongated planar body section and a distal head section depending angularly from the plane of the body section at an angle of between 0° and 90° relative to the plane thereof. Preferably, the distal head section depends from the body section at an angle of approximately 45°.

The retractor assembly includes a center retractor blade, an upper retractor blade, and a lower retractor blade, each blade being pivotally connected to one another by a pin. Camming means are operatively connected to the upper and lower retractor blades and include corresponding upper and lower cam beams which may be fixedly mounted within the tubular portion of the instrument adjacent the distal end thereof. The upper cam beam includes an upper camming slot defined therein, while the lower cam beam has a corresponding lower camming slot defined therein. The slots are symmetrically disposed ;relative to one another for facilitating a fan-like deployment of the retractor assembly. Camming pins are associated with the upper and lower cam blades for movement relative to the camming slots. A rod member is provided for operatively connecting the center retractor blade to the handle assembly.

In preferred embodiments of the invention, the handle assembly includes manipulating means comprising a rotatable driving screw mounted relative to the handle assembly and an axially moveable sleeve member which is threadably associated with the driving screw. Rotation of the driving screw causes corresponding axial movements of the sleeve member. Preferably, the sleeve member is connected to the center retractor blade by the rod member so that movements of the sleeve member will cause manipulation of the retractor assembly. Alternatively, the manipulating means may comprise a driving screw mounted for axial translation relative to the handle assembly in response to rotation of a sleeved knob member.

BRIEF DESCRIPTION OF THE DRAWINGS

The foregoing objects and other features of the invention will become more readily apparent and may be understood by referring to the following detailed description of preferred embodiments, taken in conjunction with the accompanying drawings forming a part hereof.

FIG. 12 is a top view of a handle in accordance with a preferred embodiment of the present invention.

FIG. 13 is a side view of a handle taken along line 13—13 of FIG. 12.

FIG. 14 is an unfolded end view of a proximal end of the handle of FIG. 12 incorporating progressive stops in the camming surfaces.

FIG. 15 is a side view in cross section of the rotation knob.

FIG. 19 is a side view in cross section of a handle assembly in accordance with a preferred embodiment of the present invention.

FIG. 20 is a side view of a barrel cam structure for use in the handle assembly of FIG. 19.

FIG. 21 is an end view of the barrel cam of FIG. 20 taken along line 21—21.

FIG. 22 is a side view of a barrel cam structure having progressive stops formed into the camming surfaces.

FIG. 25 is a side view in partial cross section of a preferred embodiment of a closed surgical retractor in accordance with the present invention.

FIG. 26 is a side view in partial cross section of the surgical retractor of FIG. 25 with the retractor blades in the deployed position.

FIGS. 27–29 show preferred embodiments of retractor blades for use with the present invention.

FIG. 30 is a side view in partial cross section of a preferred embodiment of an open surgical retractor in accordance with the present invention.

FIG. 31 is a side view of the retractor assembly of the surgical retractor of FIG. 30 in the closed position.

FIG. 32 is a top view of the retractor assembly having a blunt end.

FIG. 33 is a side view of the retractor assembly of FIG. 32 through line 33—33.

FIG. 34 is a side view of the retractor assembly having a hollow end.

FIG. 35 is a top view of the retractor assembly of FIG. 34 taken through line 35–35.

FIG. 36 is a perspective view of a preferred embodiment of the retractor assembly in the closed position.

FIG. 37 is a perspective view of the retractor assembly of FIG. 36 in the deployed position.

FIG. 38 is a perspective view of a preferred embodiment of the retractor assembly in the closed position.

FIG. 39 is a perspective view of the retractor assembly of FIG. 38 in the deployed position.

FIG. 40 is a perspective view of a preferred embodiment of the retractor assembly in the closed position.

FIG. 41 is a perspective view of the retractor assembly of FIG. 40 in the deployed position.

FIG. 44 is a perspective view in partial cross-section of the surgical retractor of FIG. 42, with the retractor assembly thereof in a closed position.

FIG. 45 is a perspective view in partial cross-section of the surgical retractor of FIG. 42, with the retractor assembly thereof in a partially deployed position.

FIG. 46 is a perspective view in partial cross-section of the surgical retractor of FIG. 42, with the retractor assembly thereof in a fully deployed position.

FIG. 49 is a perspective view in partial cross-section of the surgical retractor of FIG. 48, with the retractor assembly thereof in a closed position.

FIG. 50 is a perspective view in partial cross-section of the surgical retractor of FIG. 48, with the retractor assembly thereof in a partially deployed position.

FIG. 51 is a perspective view in partial cross-section of the surgical retractor of FIG. 48, with the retractor assembly thereof in a fully deployed position.

DETAILED DESCRIPTION OF PREFERRED EMBODIMENTS

Figure 1:
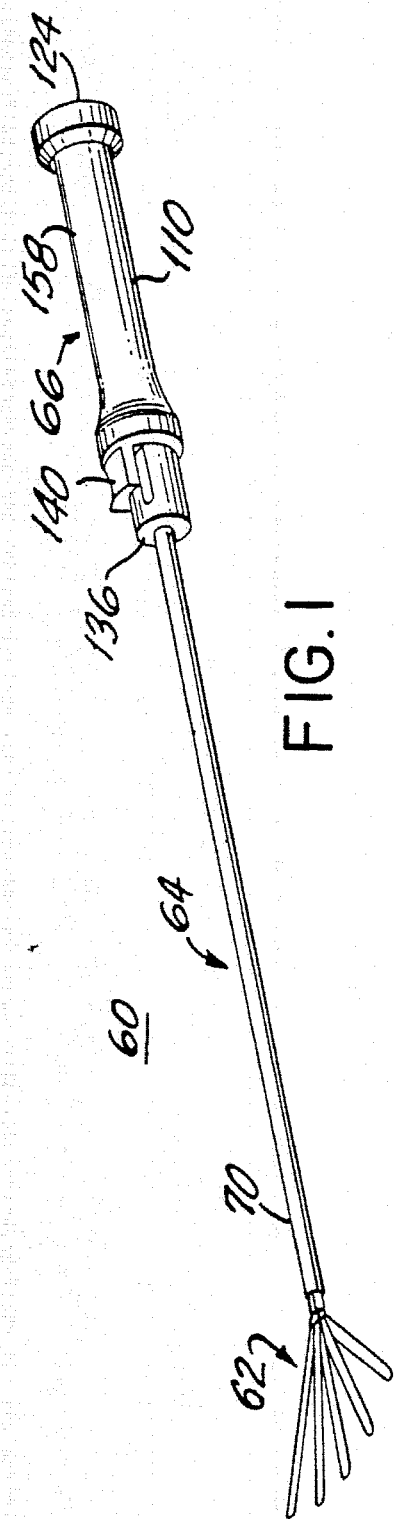
FIG. 1 is a perspective view of a preferred embodiment of the present invention.
Figure 2:
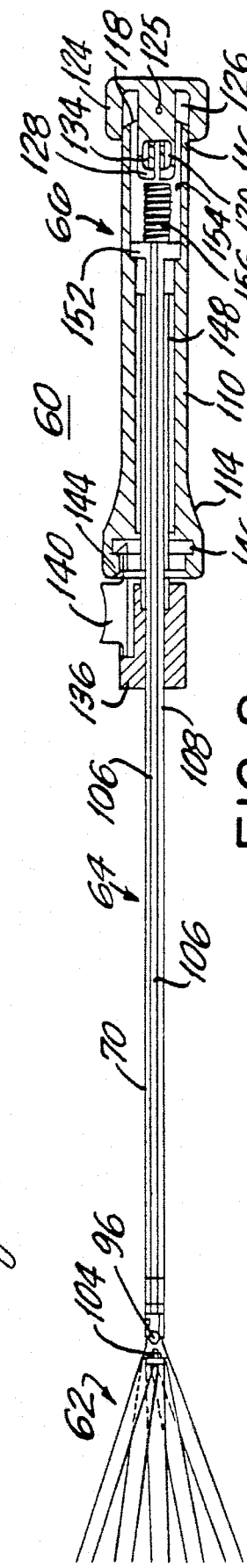
FIG. 2 is a side view in cross section of a preferred embodiment of the present invention with the retractor blades deployed in a fan configuration.
Figure 3:
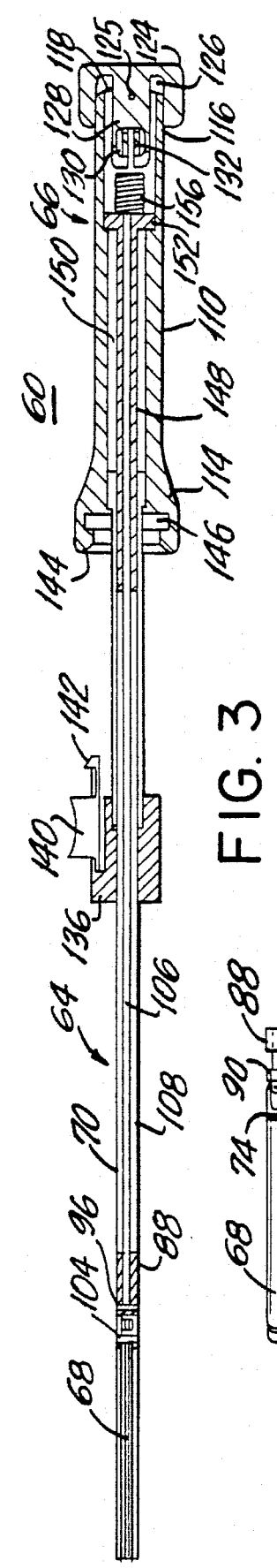
FIG. 3 is a side view in cross section of a preferred embodiment of the present invention with the retractor blades folded and enclosed by an enclosure tube.

Referring now in specific detail to the drawings, in which like reference numbers identify similar or identical elements, FIGS. 1–3 illustrate a preferred embodiment of a surgical retractor, shown generally at 60. The retractor 60 can be broken down into a retractor assembly 152, elongated tubular housing means 64 and handle means 66. The embodiment of FIGS. 1–3 is adapted for and particularly useful in endoscopic or laparoscopic procedures wherein at least an endoscopic portion of the surgical retractor 60 is inserted into the operative site through a cannula (not shown).

Figure 4:
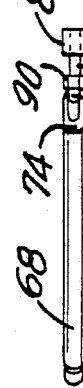
FIG. 4 is a side view of the retractor blades and the reciprocal yoke assembly for the surgical retractor of FIGS. 1–3.
Figure 5:
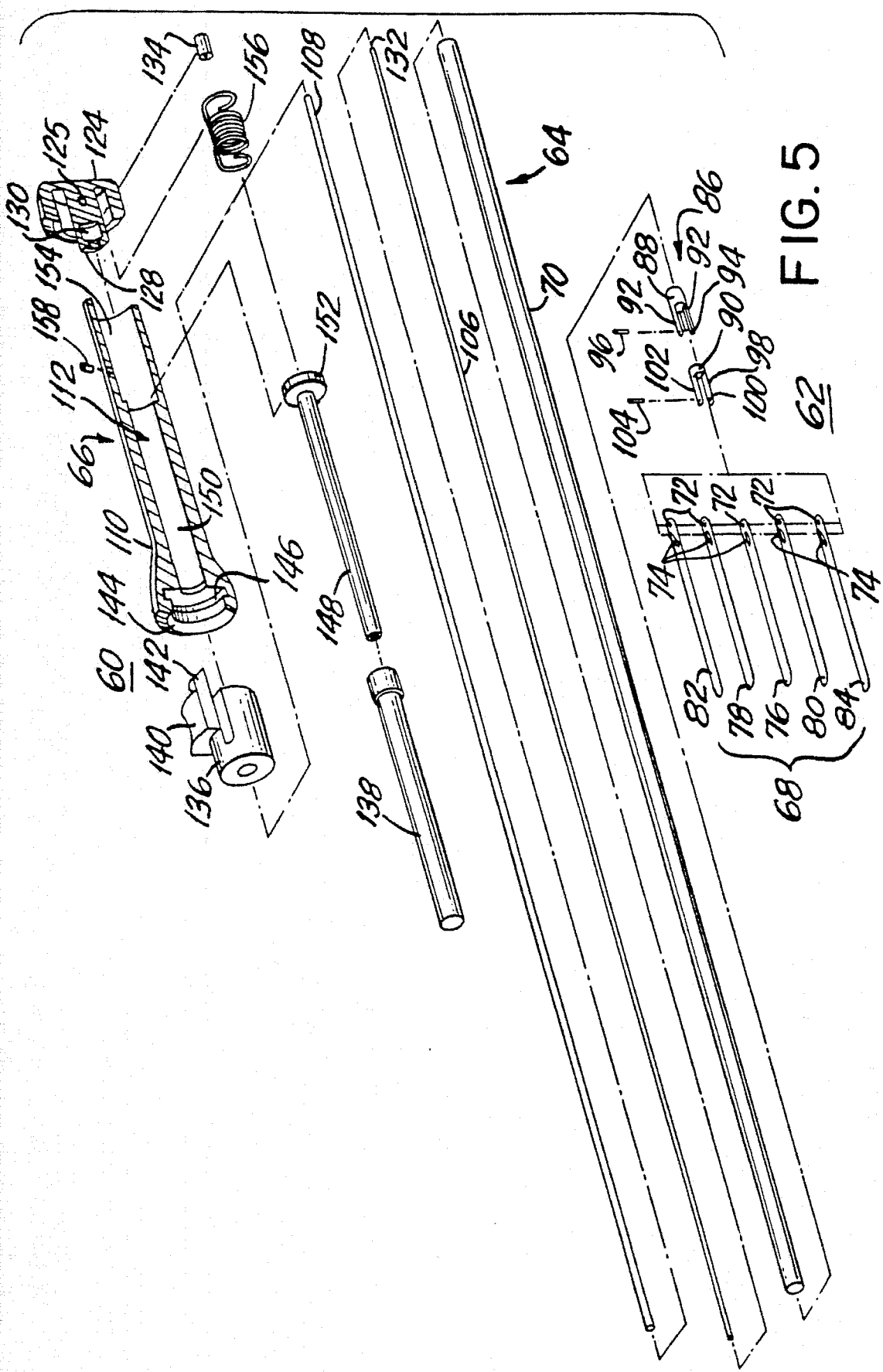
FIG. 5 is an exploded perspective view of a preferred embodiment of the present invention.
Figure 6:
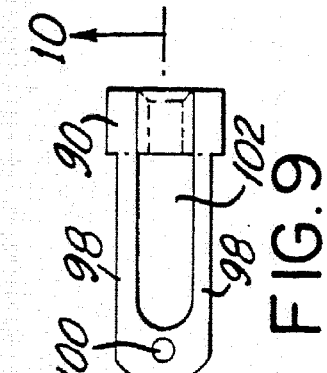
FIG. 6 is a top view of the pivot yoke assembly for a preferred embodiment of the present invention.
Figure 7:
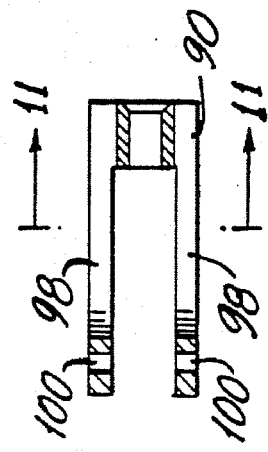
FIG. 7 is a side view of the pivot yoke assembly taken through line 7—7 of FIG. 6.
Figure 8:
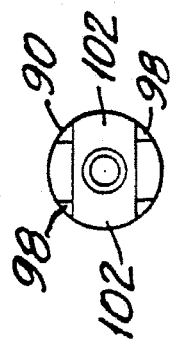
FIG. 8 is an end view of the pivot yoke assembly taken through line 8—8 of FIG. 7.

The retractor assembly 62 generally comprises a plurality of interleaved elongated blades 68 disposed in stacked relation and pivotally deployable about a proximal end to form an interleaved fan configuration (FIG. 2). This fan configuration can be readily adapted to different shapes and uses by either varying the number or size of the blades 68 or their respective angles of deployment. In the closed stacked position, the blades 68 fold in upon each other in axial alignment (FIGS. 3 and 4). In the embodiment of FIGS. 1–3, the retractor assembly 62 is contained within an enclosure tube 70 prior to deployment (FIG. 3) as will be discussed in greater detail below.

Referring to FIGS. 5–11, each of the blades (collectively referred to as 68) of the retractor assembly is provided with a fixed pivot hole 72 in a proximal end thereof. A camming slot 74 is located distal to the pivot hole 72 and is formed at predetermined angles to effect proper deployment of the retractor assembly 62. In the embodiment of FIGS. 1–5, for example, center blade 76 is provided with an axially aligned camming slot to maintain the blade in a fixed axial orientation. The blades positioned adjacent center blade 76, i.e. blades 78, 80, cam outward in opposing directions to a predetermined angle with respect to the longitudinal plane of the center blade 76. Similarly, the outward most blades, i.e. 82, 84, have camming slots which cause the blades to move in opposing directions to a predetermined angle greater than that of blades 78 and 80 so as to form a fan configuration which deploys outward respectively from the center blade 76.

Figure 9:
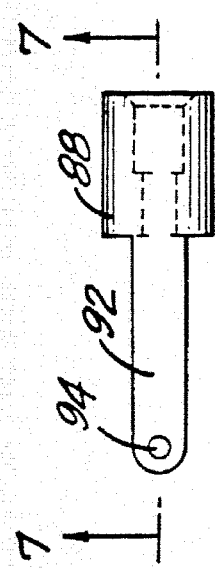
FIG. 9 is a top view of the slide yoke assembly for a preferred embodiment of the present invention.
Figure 10:
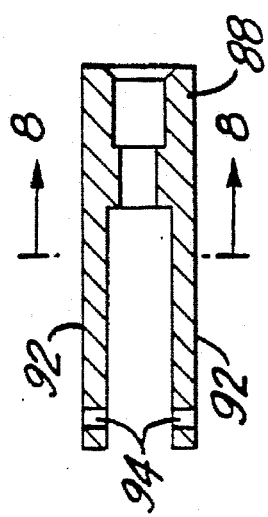
FIG. 10 is a side view of the slide yoke assembly taken through line 10—10 of FIG. 9.
Figure 11:
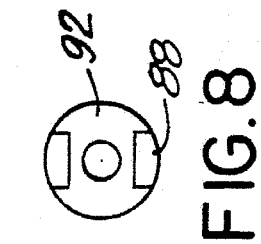
FIG. 11 is an end view of the side yoke assembly taken through line 11—11 of FIG. 10.

Blades 68 are interconnected by a unique reciprocal yoke assembly 86 (FIGS. 5–11) including a pivot yoke 88 (FIGS. 6–8) and a slide yoke 90 (FIGS. 9–11). Referring to FIGS. 5–8, pivot yoke 88 includes a pair of parallel axially extending arms 92 containing a transverse bore 94 in a distal end thereof. Pin 96 extends through transverse bore 94 and each of the fixed pivot holes 72 formed in the proximal ends of blades 68. Thus blades 68 are free to pivot about pin 96 in pivot yoke 88.

Slide yoke 90 includes a pair of axially extending parallel arms 98, each having a transverse bore 100 formed in a distal end thereof. Each parallel arm 98 is further provided with a longitudinal channel 102 adapted and configured to receive parallel arms 92 of the pivot yoke 88 therein. Pin 104 extends through transverse bore 100 and camming slots 74 in blades 68. As the pivot yoke 88 and slide yoke 90 move reciprocally relative to one another in channel 102, the movement of pin 104 in camming slots 74 effects the deployment and closure of blades 68.

Referring to FIGS. 1–3 and 5, elongated tubular housing means 64 includes a center rod 106 disposed within a guide tube 108. In the present embodiment, an enclosure tube 70 serves to at least partially enclose the combined center rod 106 and guide tube 108. Slide yoke 90 is provided with an axial bore 110 for fixedly receiving a distal end of center rod 106. Pivot yoke 88 has an axial bore 112 aligned with bore 110 to permit center rod 106 to reciprocally move slide yoke 90 with respect to pivot yoke 88. Pivot yoke 88 is fixed to the distal end of guide tube 108 (FIG. 5) and serves to pivotally hold blades 68 in place.

Referring now to FIGS. 5 and 12–15, handle means 66 comprises an axially aligned, substantially cylindrical housing 110 having a central bore 112 extending from a proximal end 114 to a distal end 116. At the proximal end, a helical camming surface 118 is provided with integral stopping tabs 120. See FIGS. 12–14. Where desired, intermediate grooves 122 may be formed in the helical camming surface 118 to provide sequential stops in the deployment of the retractor assembly 62. See FIG. 14.

Deployment knob 124 (FIG. 15) interfits into the distal end 116 of cylindrical housing 110 with the helical camming surface 118 at least partially contained in annular channel 126. A center projection 128 contains a cavity 130 for receiving and securing a proximal end 132 of center rod 106. Capping element 134 attaches to end 132 and is adapted to be securely retained within cavity 130 while allowing deployment knob 124 to rotate. A transverse camming pin 125 is mounted in deployment knob 124 with a portion of the pin 125 extending into annular channel 126 to engage helical camming surface 118.

A clasp knob 136 is fixed to outer bushing 138 and serves to retract and extend enclosure tube 70. Both clasp knob 136 and outer bushing 138 are fixed to enclosure tube 70 and move axially reciprocally therewith to cover and uncover the retractor assembly 62. Clasp knob 136 is provided with a transversely flexible locking member 140 having a hooked locking tab 142 attached thereto. This locking tab 142 is adapted to be transversely caromed by flange 144 in housing 110 and to abut and engage an inner surface 146 of flange 144. See FIGS. 2, 3 and 5.

Outer bushing 138 telescopically engages inner bushing 148 and is axially movable along the inner bushing 148. A cylindrical cavity 150 is formed in housing 110 to accommodate both the inner bushing 148 and the outer bushing 138. Inner bushing 148 is provided with a flange 152 at a proximal end, which flange 152 travels axially in cavity 154 in a proximal end of housing 110. An extension spring 156 is disposed in cavity 154 between flange 152 and center projection 128 of deployment knob 124. This extension spring 156 serves to apply an axial distal force on the flange 152 of inner bushing 148 which force is transmitted through the flange to center projection 128 of deployment knob 124. This axial distal force maintains pressure on camming pin 125 against helical cam 118. A set screw 158 is provided in housing 110 to limit travel of flange 152 in cavity 154.

To deploy the retractor assembly 62 of this embodiment of the present invention from the closed position (FIG. 3), clasp knob 136 is moved proximally until hooked locking tab 142 just abuts flange 144. At this point, the proximal end of outer bushing 138 abuts flange 152 of inner bushing 148 and the hooked locking tab 142 of transversely flexible locking member 140 engages inner surface 146 of flange 144 thus locking enclosure tube 70 in the retracted position. See FIG. 2.

Thereafter, deployment knob 124 is rotated, driving transverse camming pin 125 along helical camming surface 118 formed in the proximal end 114 of cylindrical housing 110. This action moves deployment knob 124 proximally with respect to cylindrical housing 110 and drawing center rod 106 in a proximal direction with respect to guide tube 108. As center rod 106 moves proximally, pivot yoke 86 retracts in channels 102 of slide yoke 90 causing pin 96 to cam in camming slots 74 of retractor blades 68 which, simultaneously pivot in a predetermined configuration about pin 104 in slide yoke 90.

Closure of the retractor assembly 62 is accomplished simply by rotating deployment knob 124 in the opposite direction to bring blades 68 into a stacked interleaved position. Transversely flexible locking member 140 is depressed to disengage hooked locking tab 142 from the inner surface 146 of flange 144. Thereafter, transversely flexible locking tab 142 is moved distally until enclosure tube 70 covers at least a portion of the closed retractor assembly 62. See FIG. 3.

Figure 16:
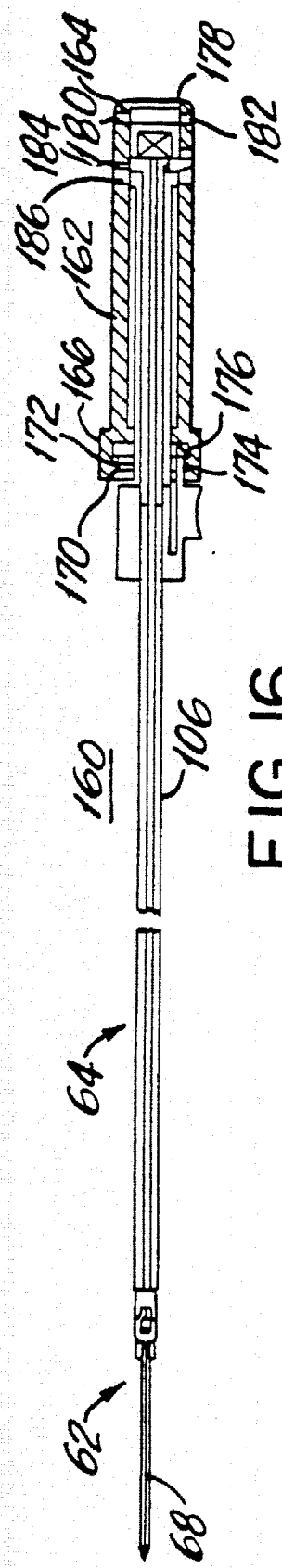
FIG. 16 is a side view in cross section of a surgical retractor in accordance with a preferred embodiment of the, present invention.
Figure 17:
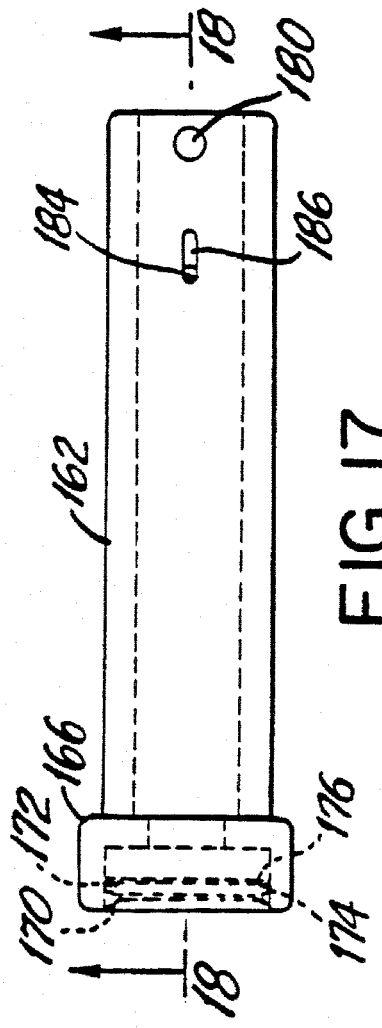
FIG. 17 is a top view of a handle in accordance with the surgical retractor of FIG. 16.
Figure 18:
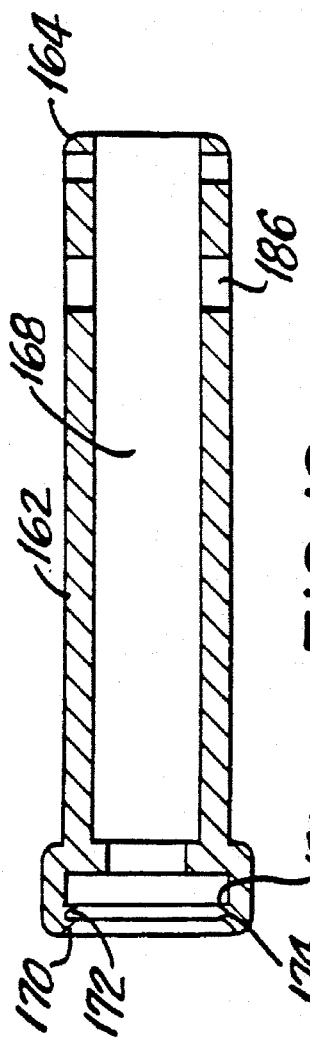
FIG. 18 is a side view of a handle taken along line 18—18 of FIG. 17.

Referring to FIGS. 16–18, a variation of the embodiment of the surgical retractor of FIGS. 1–16 is shown. The surgical retractor, shown generally at 160, includes the same basic subgroups discussed above including a retractor assembly 62, an elongated tubular housing means 64 and a handle means 66.

The retractor assembly 62 and the elongated tubular housing means 64 are substantially similar in construction and operation as those of the surgical retractor 60 discussed above. Handle means 66, however, differs in some structural aspects. A cylindrical housing 162 having a proximal end 164 and a distal end 166 with a central bore 168 therethrough is provided. The bore 168 is restricted in size near distal end 166 of housing 162 and is substantially open at the proximal end 164. See FIG. 18. A pair of annular flanges 170, 172 are axially sequentially disposed in the distal end 166 of housing 162, each such flange defining a respective inner surface 174, 176. Inner and outer bushings, 148 and 138 respectively, are configured and operate substantially the same as those described above with respect to FIGS. 1–15. Center rod 106, however, is fixed to disk 178 which is anchored in the opening 180 in the proximal end 164 of housing 162 by means of set screws 180, 182. A compression spring 156 is disposed between flange 152 of inner bushing 148 and disk 178 and, when compressed, imparts a distal axial force to move clasp knob 136 and the attached enclosure tube 70 distally. Flange 152 is limited in axial movement by pin 184 extending transversely from the outer edge of flange 152 into axial slot 186.

To deploy the retractor assembly 62 of this surgical retractor 160 from the closed position, clasp knob 136 is moved in a proximal direction exposing retractor assembly 62. Hooked locking tab 142 of transversely flexible locking member 140 engages the inner surface 174 of distal most annular flange 170 effectively locking enclosure tube 70 in its most proximal position. Continued proximal motion of clasp knob 136 causes outer bushing 138 to engage inner bushing 148 and move inner bushing proximally with respect to center rod 106. This motion causes the retractor assembly 62 to deploy in a manner substantially the same as that set forth above with respect to the embodiment of FIGS. 1–15. At its proximal most position, the hooked locking tab 142 of transversely flexible locking member 140 engages the inner surface 176 of proximal most annular flange 172 thus locking the blades 68 in a deployed fan configuration.

Referring now to FIGS. 19–22, further variation of the handle means of the preferred embodiment of FIGS. 1–15 is shown. The handle means 188 includes a cylindrical housing 190 having a proximal end 192 and a distal end 194 with a central bore 196 therethrough. A clasp knob 136 attached to an outer bushing 138 and an enclosure tube 70 serves to effect proximal and distal motion of the enclosure tube in substantially the same way as that described above. An inner bushing 148 connects to guide tube 108 and has an axial bore 198 disposed therein to allow passage of center rod 106. Movable block 200 engages and holds a proximal end of center rod 106 for limited axial reciprocal motion. A transverse camming pin 202 extends through movable block 200 and travels axially in slots 204, 206 formed in cylindrical housing 190.

Deployment of the retractor assembly 62 is accomplished by means of a fan adjust collar 208 having a flange 210 in a distal end and a barrel cam slot 212 in a proximal end interconnected by a drive tube 214. Barrel cam slot 212 may either provide a smooth progression (FIG. 20) or may utilize intermediate grooves 216 (FIGS. 22) to give intermediate stops as the blades 68 deploy. A compression spring 218 is disposed between inner bushing 148 and movable block 200 in order to preload the system and to assist in distal movement of enclosure tube 70.

In operation, hooked locking tab 142 of transversely flexible locking member 140 is moved proximally until tab 142 engages and locks in place behind flange 210 in fan adjust collar 208. In this position, enclosure tube 70 is located at its proximal most position exposing the retractor assembly 62. Fan adjust collar 208 is then rotated relative to cylindrical housing 190 causing transverse camming pin 202 to be driven axially distally by barrel cam slot 212 in slots 204, 206. This relative axial distal motion deploys blades 68 into a fan configuration.

To close the retractor, fan adjust collar 208 is rotated in the opposite direction to move the blades 68 together. Transversely flexible locking member 140 is depressed to disengage hooked locking tab 142 from flange 210. Compression spring 218 assists in the distal movement of enclosure tube 70. Clasp knob is then moved distally until enclosure tube 70 is at its distal most position enclosing at least a portion of retractor assembly 62.

FIGS. 25–29 illustrate a surgical retractor, indicated generally at 220, utilizing a pistol grip-type handle means 222 and an abbreviated retractor assembly 224. The handle means 222 includes a stationary housing 226 with a depending finger grip 228 integrally formed therewith, and a pivotal arm 230 having a depending finger grip 232 on a proximal end thereof and a rack 234 formed on a distal end. Pivotal arm 230 attaches to stationary housing 226 by means of a pivot pin 236. Both the depending finger grip 228 of the stationary housing 226 and the depending finger grip 232 of pivotal arm 230 have provided thereon complementary inward facing racks, 238, 240 respectively, whose teeth 242 progressively interlock to hold pivot arm 230 at a predetermined angular orientation with respect to stationary housing 226.

A longitudinal cavity 244 is provided in an upper portion of stationary housing 226 to accommodate the reciprocal longitudinal motion of bolt assembly 246. This bolt assembly comprises a proximally mounted cylindrical pinion 248 followed distally by a mounting block 250 for fixedly holding center rod 252. A guide tube mounting block 254 is attached distally to mounting block 250 and includes a bolt handle 256 fixed to the guide tube mounting block 254 which handle 256 is guided in axial movement by slot 258 formed in stationary housing 226. Guide tube mounting block 254 is provided with an axial bore 260 therethrough to allow center rod 252 to be driven distally by the interaction of rack 234 and cylindrical pinion 248 as described below.

An endoscopic enclosure tube 262 is fixed to stationary housing 226 and serves to enclose and protect the retractor assembly 224 when it is closed and retracted. Guide tube 264 extends from guide tube mounting block 254, through enclosure tube 262 to attach to a pivot yoke assembly 90 as described above. Center rod 252 extends from mounting block 250, through axial bore 260 and guide tube 264 to attach to slide yoke assembly 88. A rotation knob 265 is rotatably mounted in stationary housing 226 and engages guide tube 264 so as to allow direct rotation of the retractor assembly 224.

The abbreviated retractor assembly 224 operates in a manner similar to that described above with respect to retractor assembly 62, and includes an axial blade 266 (FIG. 29) connected at a proximal end to center rod 252. A pair of angularly deployable blades 268, 270 with serrated longitudinal side edges 272, 274 cooperate with axial blade 266 to assist in the retractor function. Axial blade 266 is texturized along its flat surfaces 276 to assist in gripping and retracting tissue. Blades 268, 270 are provided with a pivot hole 278 in a proximal end and a camming slot 280 located distally to pivot hole 278. A pivot pin 282 mounted in pivot yoke assembly 88 passes through pivot holes 278 and acts as a pivot point for blades 268 and 270. A camming pin 284 is transversely mounted in axial blade 266 (FIG. 29) and rides in camming slots 280 to angularly deploy blades 268 and 270 as the axial blade 266 is reciprocally moved with respect to pivot yoke assembly 88. An axial slot 283 is provided in axial blade 266 proximal to transverse camming pin 284. This slot 283 allows axial blade 266 to move reciprocally with respect to pivot pin 282. A compression spring 286 is disposed between the distal end of axial blade 266 and pivot yoke assembly 88 and is compressed upon deployment of the retractor assembly 224. This compressed force assists in the closure of the blades 268, 270 when the force is released.

To operate surgical retractor 220, bolt handle 256 is moved distally in slot 258 thus moving bolt assembly 246 forward. This action moves the abbreviated retractor assembly 224 out of the distal end of enclosure tube 262 and concurrently engages cylindrical pinion 248 with rack 234. See FIG. 26. Finger grips 228, 232 are approximated about pivot pin 236 causing rack 234 to drive cylindrical pinion 248 in a proximal direction drawing axial blade 266 proximally relative to pivot yoke assembly 88. Blades 268 and 270 are thus deployed by the motion of cam pin 284 in camming slots 280. Complementary racks 238 and 240 interlock to maintain the blades in a deployed attitude.

To close the retractor 220, teeth 242 of racks 238, 240 are disengaged and, with the assistance of compression spring 286, finger grips 228, 232 are moved apart until rack 234 disengages from cylindrical pinion 248. Bolt assembly 246 can then be drawn proximally to retract the closed blade assembly into enclosure tube 262.

Figure 23:
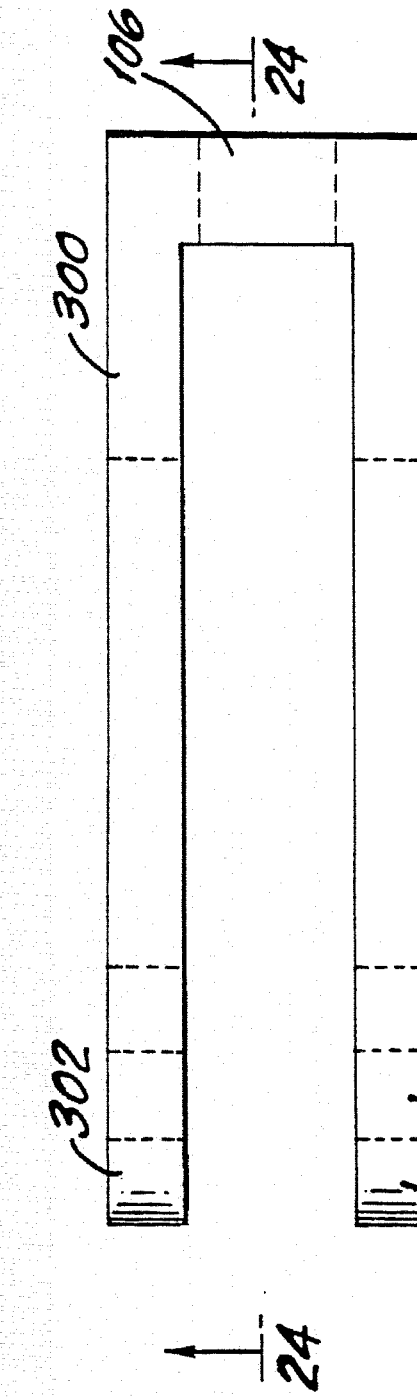
FIG. 23 is a side view of a pivot yoke in accordance with a preferred embodiment of the present invention.
Figure 24:
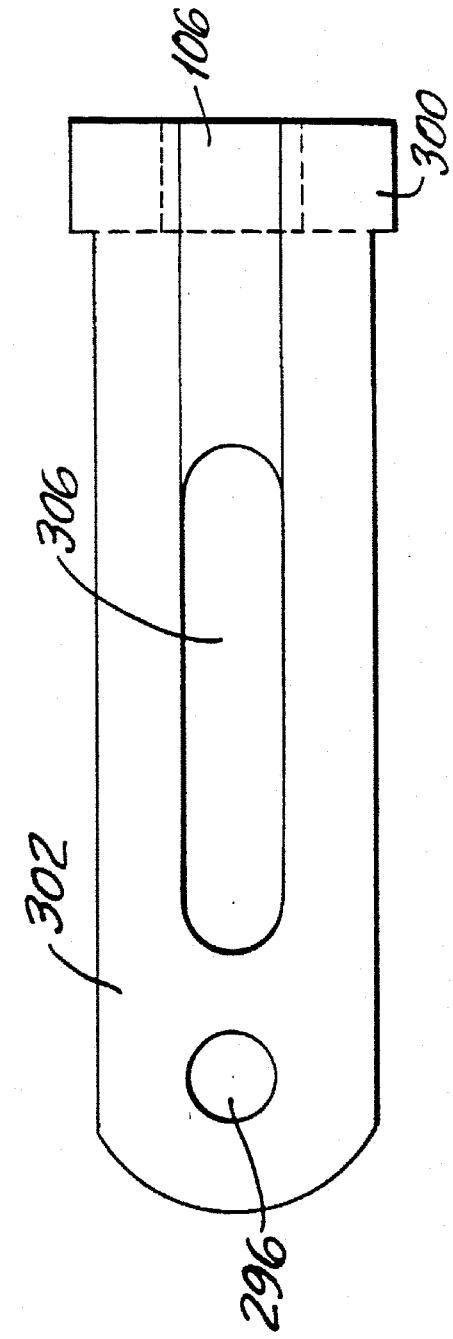
FIG. 24 is a top view of a pivot yoke taken along line 24—24 of FIG. 23.

Referring to FIGS. 23, 24 and 30–40 and specifically to FIG. 30, a surgical retractor 288 is shown in accordance with a simplified embodiment of the present invention. The surgical retractor 288 includes a retractor assembly 290 having a housing member 292 with a blade storage cavity 294 formed in a distal end. A transverse bore 296 is formed in a proximal end of housing member 292 and serves to retain pivot pin 298 therein. Referring to FIGS. 23 and 24, a slide yoke assembly 300 interconnects with a distal end of center rod 106 and includes a pair of axial legs 302 with an aligned transverse bore 304 and an aligned, axial slot 306 formed therein. A moving pin 308 is disposed in transverse bore 304 and axial slot 306 serves to enclose pivot pin 298 and permit axial reciprocal motion of the slide yoke assembly 300 relative to pivot pin 298.

A blade assembly 310 is disposed in retractor assembly 290 and includes a pair of inner blades 312 and a pair of outer blades 314. Each of said blades 312, 314 include a pivot bore 316 formed in a proximal end and a cam slot 318 positioned distal to the pivot bore 316. In the embodiment of FIG. 30, the outer edges of blades 312, 314 are provided with serrations 320 to assist in the retractor function. Other modifications including texturized coatings, abrasive surfaces, etc. could also be utilized and are within the scope of the present invention.

Blades 312, 314 are retained in blade storage cavity 294 with pivot pin 298 positioned in pivot bores 316. Moving pin 308 of slide yoke assembly 300 is disposed in cam slots 318 such that reciprocal axial motion of slide yoke assembly 300 relative to housing member 294 causes moving pin 308 to move in cam slots 318 to either deploy or retract blades 312, 314 about pivot pin 298.

An elongated tubular housing assembly 322 is connected to retractor assembly 290 and includes a center rod 106 and a guide tube 108. Center rod 106 extends through guide tube 108 and is connected at a distal end to slide yoke assembly 300 and at a proximal end to handle means 324. Guide tube 108 is attached at a distal end to housing member 292 and at a proximal end to handle means 324. In this embodiment of surgical retractor 288, guide rod 106 is axially fixed in handle means 324. Center rod 106 is adapted for axial reciprocal motion within guide tube 108.

Handle means 324 includes a stationary handle 326 and a pivoting handle 328. Finger loops 330, 332 are provided on the lower ends of handles 326, 328 respectively. Where desired, racks 329, 331 may be provided with the handles 326, 328 as discussed above in order to lock the retractor assembly 290 at a predetermined degree of deployment.

Pivoting handle 328 is pivotally mounted to stationary handle 326 by pivot pin 334. A pivot bushing 336, comprising a pair of disks 338 each having connecting means for interengaging the disks 338 with each other, captures a proximal end of center rod 106 to control axial motion thereof. This pivot bushing 336 retains the proximal end of center rod 106 while permitting the rod 106 to freely rotate therein and maintain the rod 106 in axial alignment with guide tube 108 throughout the entire range of motion of pivoting handle 328.

In preferred embodiments, as shown in FIG. 30, the retractor assembly 290 and the elongated tubular housing assembly 322 are axially rotatable by rotation knob 340 mounted in stationary handle 326. This rotation knob 340 engages bushing 342 attached to guide tube 108. Rotation knob 340 is preferably knurled or provided with ridges to allow for easy manipulation by the user's thumb or fingers. Similarly, bushing 342 may be provided with angular faces of polygonal cross-section cooperating with corresponding faces formed in the stationary handle 326 so as to provide predetermined rotational stops wherein the retractor assembly 290 is maintained at a given angular orientation relative to the handle means 324.

To deploy the retractor assembly 290 of surgical retractor 288, pivoting handle 328 is moved from an initial position (shown in phantom in FIG. 30) to a final position wherein pivot bushing 336 is moved distally into close approximation with stationary handle 326. This motion drives center rod 106 distally through guide tube 108 thereby driving slide yoke assembly 300 with moving pin 308 through cam slots in blades 312, 314. Depending upon the degree of distal movement of center rod 106 relative to guide tube 108, blades 312, 314 are caused to deploy about pivot pin 298 into a fan configuration. See FIG. 30. To close the retractor assembly 290, handles 326 and 328 are approximated causing pivot bushing 336 to move proximally with respect to pivot pin 334. This proximal movement draws center rod 106 and thus moving pin 308 in a proximal direction moving blades 312, 314 into a stacked interleaved configuration in blade storage cavity 294.

Referring now to FIGS. 31–41, there is shown a wide variety of housing member configurations for retractor assemblies. In FIG. 31, housing member 292 includes a streamlined removable tip portion 346 attached at a distal end to protect blade storage cavity 294.

FIGS. 32 and 33 show a housing member 344 integrally formed with guide tube 108 wherein the distal ends are crimped over to form a blunt rectangular end 348 distal to blade storage cavity 294. A transverse bore 304 is formed in housing member 344 to receive stationary pivot pin 298. Aperture 350 serves as an attachment point for bushing 342 to permit rotation of guide tube 108 by rotation knob 340. Similarly, FIGS. 34 and 35 show a housing 344 integrally formed with guide tube 108 with a distal end 352 formed in a blunt cylindrical shape. A transverse bore 304 is formed proximal to blade storage cavity 294 and an aperture 350 interconnects guide tube 108 with bushing 342.

FIGS. 36 and 37 show a closed end housing member 354 having a rounded distal portion 356 with a rectangular cross-section. Proximal to rounded distal portion 356, upper and lower surfaces 358, 360 of housing member 354 are substantially flattened and then ramp out to conform in diameter and cross-section with guide tube 108. A transverse bore 304 is formed in housing member 354 proximal to blade storage cavity 294 to receive pivot pin 298 therein. Blades 362 pivot about pivot pin 298 between a closed position (FIG. 36) and a deployed position (FIG. 36) as described above.

FIGS. 38 and 39 show a streamlined closed end housing member 364 having a configuration somewhat similar in appearance to that of housing 292 of FIG. 31 with the exception that streamlined tip portion 346 is monolithically formed with housing member 364. This embodiment is otherwise similar in operation to that of closed end housing member 354 described above.

Referring to FIGS. 40 and 41, an open end housing member 366 is shown having a blade storage cavity 294 which is open at its distal end 368. Both upper and lower surfaces, 370, 372 are rounded to facilitate smooth insertion into a cannula (not shown). As in the embodiment of FIGS. 36 and 37, upper and lower surfaces 370, 372 of housing member 366 are substantially flattened near the distal end 368 and ramp out to conform in diameter and cross-section with guide tube 108. This embodiment is otherwise similar in operation to that of housing members 354 and 364 above.

Figure 42:
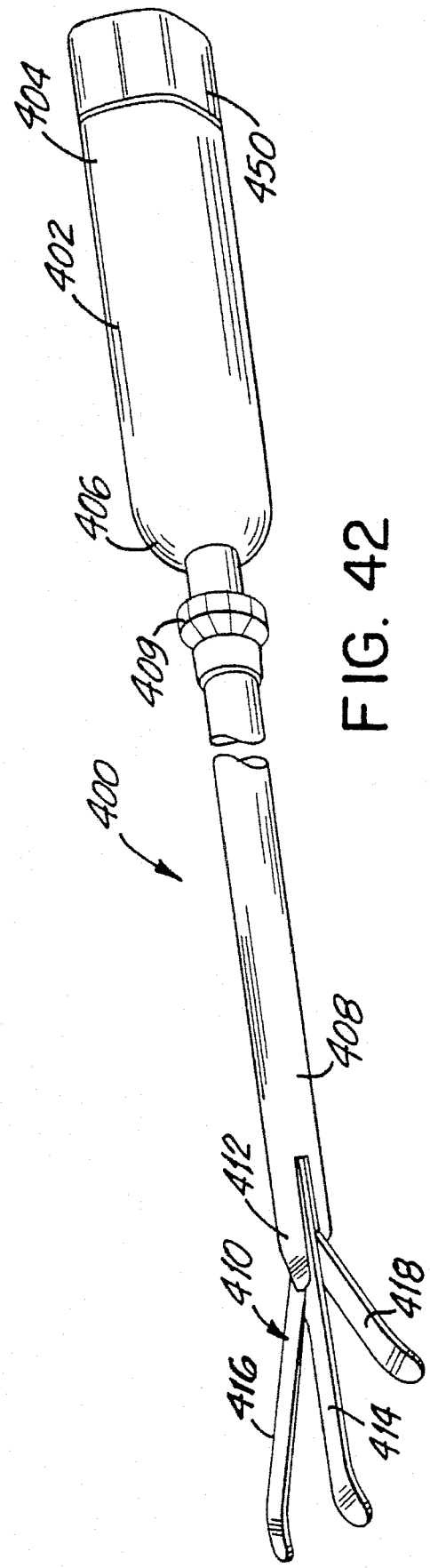
FIG. 42 is a perspective view of another preferred embodiment of the surgical retractor in accordance with the subject invention.

Turning now to FIG. 42, another embodiment 400 of the surgical retractor of the subject invention is illustrated. The surgical retractor 400 comprises a handle portion 402 having opposed proximal and distal ends 404 and 406, an elongated endoscopic portion 408 extending from the distal end 406 of the handle portion 402, and a retractor assembly 410 operatively associated with the distal end 412 of the endoscopic portion 408. A rotator cuff 409 is provided on the endoscopic portion 408 adjacent the distal end 406 of handle portion 402 for enabling a user to rotate the endoscopic portion 408 about its longitudinal axis relative to the handle portion 402. Retractor assembly 410 includes a plurality of blade members including a center blade 414, an upper blade 416, and a lower blade 418. These retractor blades will be discussed in detail hereinbelow.

Figure 43:
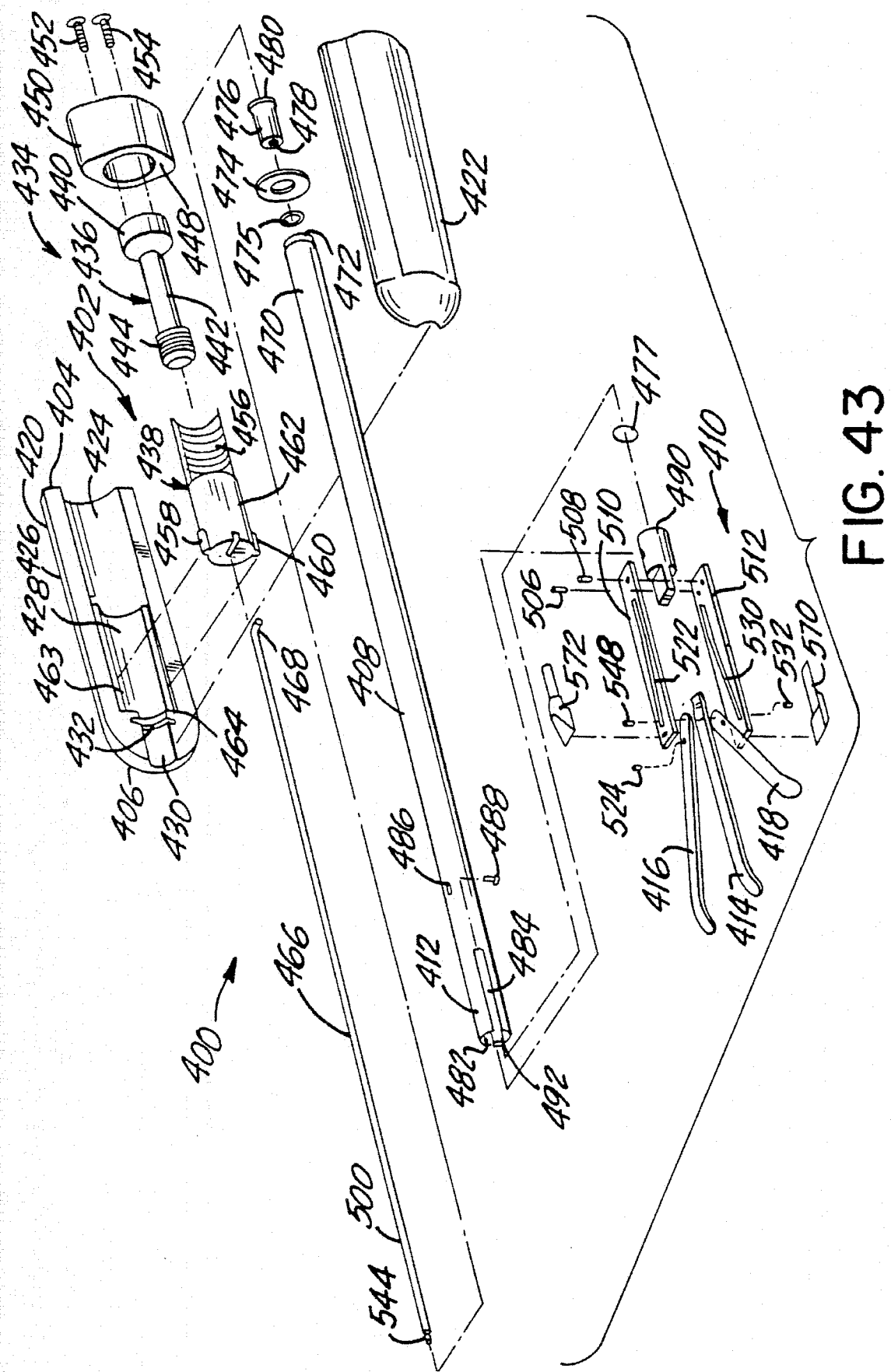
FIG. 43 is an exploded perspective view of the surgical retractor of FIG. 42.

Referring to FIG. 43, the handle portion 402 of surgical retractor 400 includes a two-part handle having hemi-sections 420 and 422. When assembled the hemi-sections 420 and 422 define a stepped axial bore 424 which extends through the handle portion 402. The axial bore 424 has a proximal chamber 426, a medial chamber 428, and a distal chamber 430 defined therein. A circumferential groove 432 is provided in the distal chamber 430. The handle portion 402 houses a driving assembly 434 which manipulates the retractor assembly 410.

Driving assembly 434 comprises a rotatable driving screw 436 and an axially movable sleeve member 438. The driving screw 436 includes a tail portion 440, a slender body portion 442, and a threaded head portion 444. The tail portion 440 is mounted within a receiving port 448 of a knob member 450 by a pair of screw type fasteners 452 and 454. The body portion 442 of the driving screw 436 is maintained within the proximal chamber 426 of the axial bore 424 of handle portion 422. The head portion 444 of driving screw 436 is threadably engaged to sleeve member 438. More particularly, the sleeve member 438 is formed with a threaded internal passage 456 which extends substantially along the length thereof. In use, rotation of the driving screw 436 causes corresponding axial translation of the sleeve member 438 relative to the handle portion 402 within the axial bore 424. The sleeve member 438 of driving assembly 434 further concludes a pair of diametrically opposed flanges 458 and 460 which are dimensioned and configured for engagement in corresponding longitudinal tracks 462 and 464 provided in the medial chamber 428 of the axial bore 424 in handle portion 402. The opposed flanges 458 and 460 function to prohibit rotation of the sleeve member 438 in response to operational rotation of driving screw 436. A notch 462 is provided in the distal end of the sleeve member 438 and is adapted and configured for lockingly engaging the end of an elongated rod member 466. Specifically, the proximal end 468 of rod member 466 is generally L-shaped and is configured so as to lockingly engage the notch 462 in sleeve member 438. This connection between rod member 466 and sleeve member 438 functions substantially to translate the axial movements of sleeve member 438 to the retractor assembly 410 which is arranged in the distal end 412 of endoscopic portion 408.

The endoscopic portion 408 of surgical retractor 400 has a proximal end 470 at which a circumferential slot 472 is formed for maintaining a flange ring 474. A plug member 476, having an axial throughhole 478, and a rear flange 480 is mountable in the proximal end 470 of the endoscopic portion 408. Once the plug member 476 has been mounted in the proximal end 470 of endoscopic portion 408, the rear flange 480 functions to maintain the flange ring 474 in the circumferential slot 472. The endoscopic portion 408 is mounted in the distal chamber 430 of axial bore 424 in such a manner so that the flange ring 474 is maintained within the circumferential groove 432. Additionally, an o-ring seal 475 is disposed in the proximal end 470 of endoscopic portion 408 for prohibiting the egress of insufflation gas therethrough from the body cavity. Similarly, an o-ring seal 477 is disposed in the distal end 412 of endoscopic portion 408 for prohibiting the egress of insufflation gas from the surgical site. The proximal end 412 of endoscopic portion 408 has diametrically opposed longitudinally extending slots 482 and 484 which are provided for accommodating the operative deployments of the retractor assembly 410. An aperture 486 is formed adjacent the distal end 412 of endoscopic portion 408 for receiving a fastening member 488. Fastening member 488 is provided for fixing a coupling member 490 within the axially passage way 492 of the endoscopic portion 408 adjacent the distal end 412 thereof. Coupling member 490 forms a base from which the retractor assembly 410 operates.

Figure 43A:
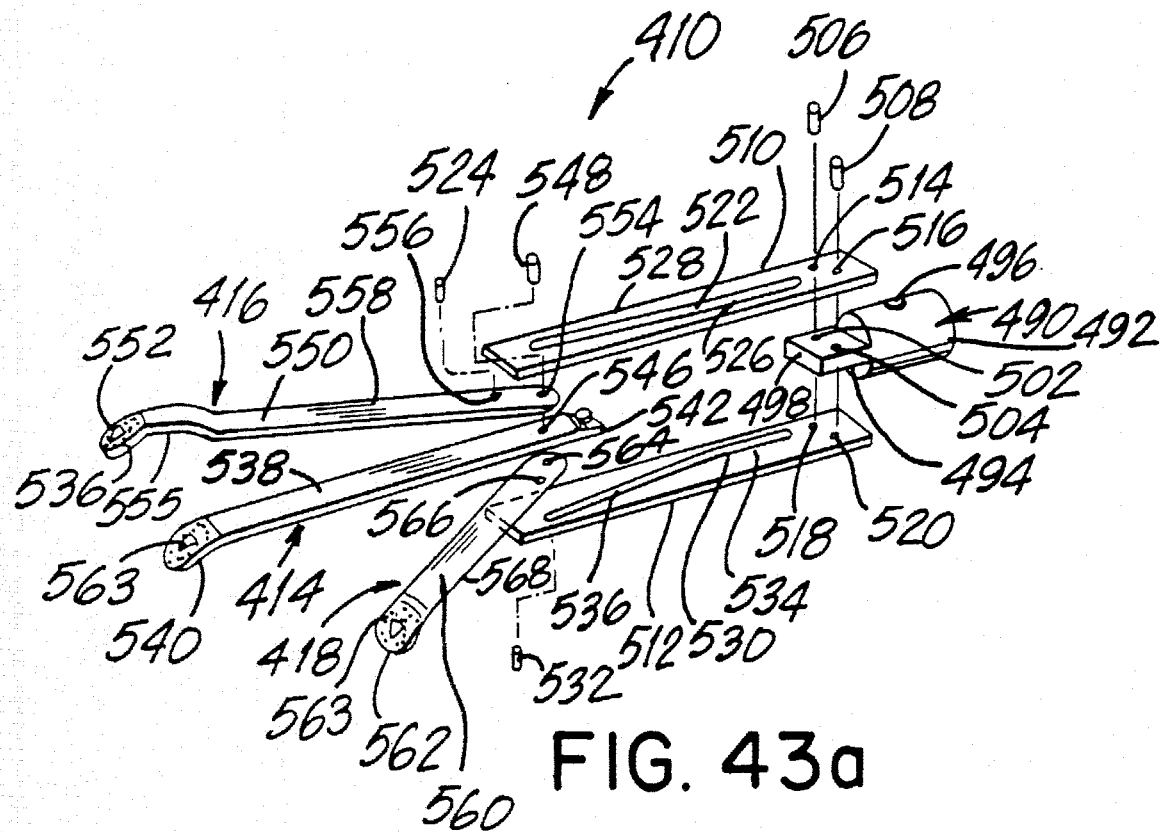
FIG. 43a is an enlarged exploded perspective view of the retractor assembly of FIG. 43.

Referring to FIG. 43a, the coupling member 490 comprises a cylindrical body section 492 and a rectangular platform section 494. The cylindrical body section 492 has a diameter which is slightly less than that of the inner diameter of the endoscopic portion 408 of surgical retractor 400. A transverse aperture 496 extends through the body section 492 for receiving fastener member 488 (FIG. 43). A longitudinal passage 498 extends through body section 492 and platform section 494 for accommodating the distal end 500 of rod member 466. The platform section 494 is provided with a pair of spaced apart transverse mounting ports 502 and 504 which extend therethrough for receiving a pair of set pins 506 and 508, respectively. More particularly, the set pins 506 and 508 mount upper and lower cam beams 510 and 512 to the platform section 494 of coupling member 490.

Upper cam beam 510 has a pair of apertures 514 and 516 and lower cam beam 512 has a pair of apertures 518 and 520 which correspond to ports 502 and 504 for receiving set pins 506 and 508. Upper cam beam 510 is formed with a camming slot 522 which defines a path in which a cam follower 524 travels. Camming slot 522 includes a proximal portion 526 which is disposed parallel to the longitudinal axis of cam beam 510 and a distal portion 528 which is disposed angularly with respect to the proximal portion 526 of camming slot 522. Similarly, the lower cam beam 512 is formed with a camming slot 530 which a defines a path in which cam follower 532 travels. Camming slot 530 includes a proximal portion 534 which is disposed parallel to the longitudinal axis of cam beam 512 and a distal portion 536 which is disposed angularly with respect to the proximal portion 526 of camming slot 522. The distal portion 536 of camming slot 522 and the distal portion 528 of camming slot 530 are symmetrically disposed relative to one another so as to facilitate a fan-like deployment configuration of the retractor assembly.

As stated briefly hereinabove, the retractor assembly 410 comprises upper and lower retractor blades 416 and 418 and a center retractor blade 414. The center blade 414 includes an elongated body portion 538 and a distal head portion 540 which depends angularly from the body portion 538 to define a paddle structure for increasing the retracting capabilities of the instrument at a surgical site. A generally T-shaped groove 542 is formed at the proximal end of the body portion 438 of center blade 414. The T-shaped groove 542 is dimensioned and configured for engagement with a slotted head 544 formed at the distal end 500 of rod member 466. (FIG. 43) An aperture 546 is provided forward from the T-shaped slot 542 for receiving a pivot pin 548.

The upper retractor blade 416 has a body portion 550 and a distal head portion 552 which depends angularly from the body portion 550, preferably at an angle of between 0° and 90°. An aperture 554 is provided in the proximal end of the body portion 550 which corresponds to aperture 546 in center retractor blade 414 for receiving the pivot pin 548. In addition, a second aperture 556 is provided forward from aperture 554, which is disposed adjacent a lateral edge 558 of blade member 416 for asymmetrically mounting cam follower 524. The upper retractor blade 416 can optionally include a bend 555 adjacent the distal head portion 552 thereof to provide additional manipulation space for center retractor blade 414, as shown for example in FIG. 43a. The lower retractor blade 418 has a body portion 560 and a distal head portion 562 which depends angularly from the body portion 560. An aperture 564 is provided in the proximal end of body portion 560 which corresponds to aperture 546 in the center blade 414 for receiving pivot pin 548. In addition, a second aperture 566 is provided forward from aperture 564, which is disposed adjacent a lateral edge 568 thereof for asymmetrically mounting cam follower 532. The retractor assembly 510 further includes a pair of opposed stabilizer heads 570 and 572 which are configured for engagement in passageway 492 of endoscopic portion 408 at the distal end 412 thereof. Referring to FIG. 43a, each of the retractor blades of retractor assembly 410 may optionally include a molded plastic cover member 563 positioned at the distal head portion thereof to provide a more blunt tip for reducing trauma to tissue during use.

Turning now to FIGS. 44–46, in operation the retractor assembly 410 of the surgical retractor 400 can be deployed from a closed position by rotating knob member 450 in the direction of indicator arrow "A", relative to the handle portion 402. As the knob 450 is rotated, the driving screw 436 rotates correspondingly. Rotation of the driving screw 436 causes axial translation of the sleeve member 438 in the direction of indicator arrow "X" in FIG. 45. Consequently, rod member 466 moves distally, urging the center retractor blade 414 of retractor assembly 410 to travel in a distal direction. From a point in time of initial movement of center blade 414, to an intermediate period of time wherein the retractor assembly 410 is in a partially deployed position, as illustrated in FIG. 45, the blades 414, 416, and 418 move as a unit, with the longitudinal axes thereof substantially in parallel alignment. This initial unitary-like movement of the retractor assembly 410 is achieved through the translation of the cam follower pins 524 and 532 within the proximal parallel portions of camming slots 522 and 530 respectively.

As rotation of the knob member 450 continues in the direction of indicator arrow "A", the sleeve member 438 continues to travel in a distal direction within the distal chamber 428 defined in handle portion 402. Accordingly, rod member 466, which is connected to sleeve member 438 urges the center retractor blade 414 forward, further causing the cam follower pins 524 and 532 to continue to move in a generally distal direction within camming slots 522 and 530, respectively. However, as the cam follower pins 524 and 532 exit the proximal portions 526 and 536 of camming slots 522 and 530, and enter the respective distal portions 528 and 536 of camming slots 522 and 530, the upper blade 416 and lower blade 418 of retractor assembly 410 begin to deploy outwardly in a fan-like manner with respect to the center blade 414, pivoting symmetrically about pin 548. The outward deployment of upper and lower retractor blades 416 and 418 continues until the cam follower pins 524 and 532 are in their distalmost positions within camming slots 522 and 530, respectively.

Figure 47:
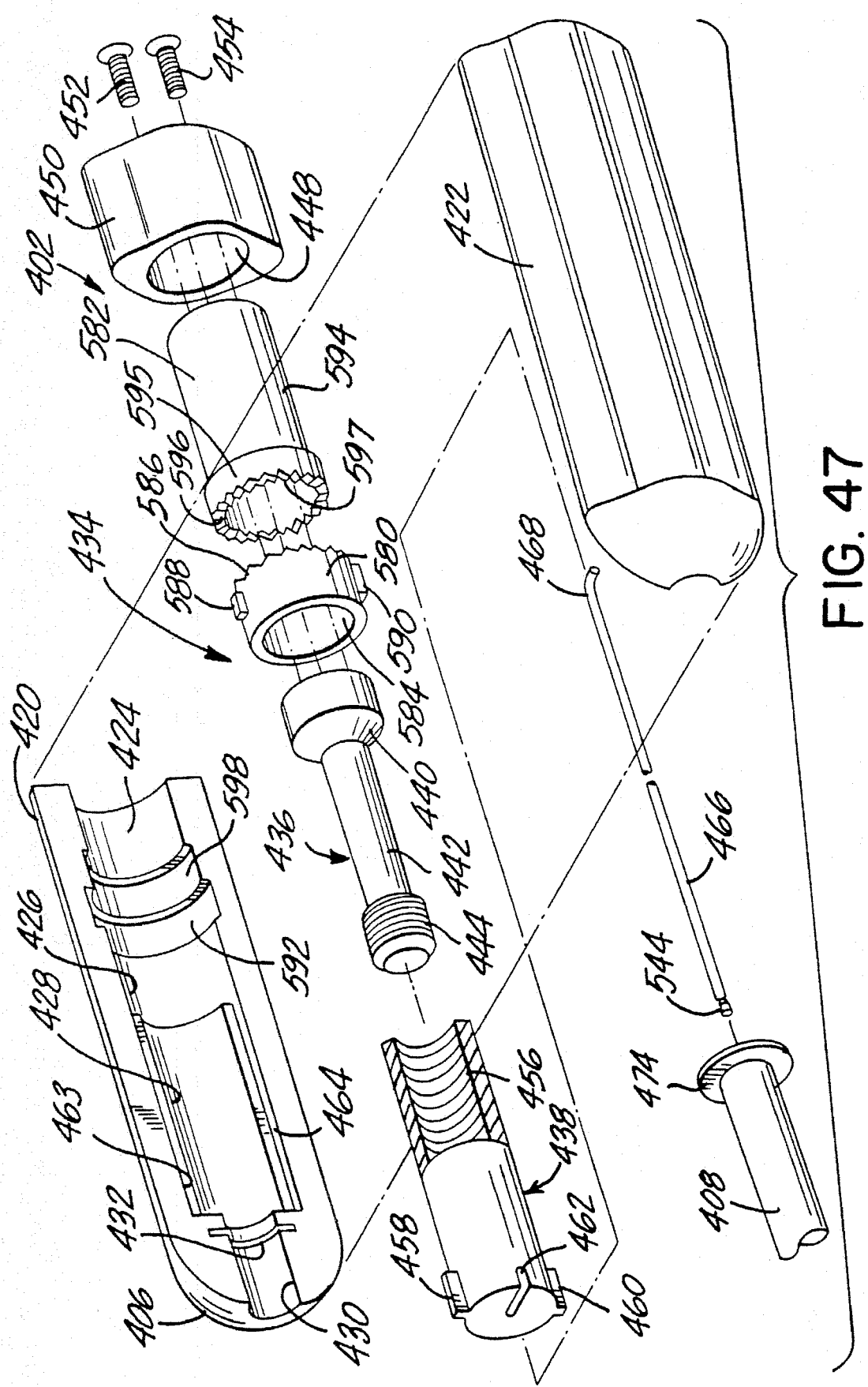
FIG. 47 is an enlarged exploded perspective view of a handle assembly for use with the surgical retractor of FIG. 42.

Turning now to FIG. 47, the driving assembly 434 of surgical retractor 400 can be provided with a position indicator mechanism consisting of cooperating ratchet members 580 and 582. This mechanism produces a detectable indication to a user that the sleeve member 438 has reached its distalmost or proximalmost position within the medial chamber 428 of axial bore 424. Ratchet member 580 defines a ring having a center passage 584 and a saw-toothed distal surface area 586. Diametrically opposed flanges 588 and 590 extend from the periphery of ratchet member 580 for maintaining ratchet member 580 within a first circumferential chamber 592 formed in the distalmost chamber 426 of handle portion 402. Ratchet member 582 has an elongated body portion 594 which is engageable within the receiving port 448 of knob member 450. A circumferential head portion 595 is formed at the distal end of body portion 594 which has a saw-toothed surface 596 for cooperating with the saw teeth 586 on ratchet member 580. An axial passage 597 extends through ratchet member 582 for accommodating the driving screw 436 of driving assembly 434. A second circumferential groove 598 is provided in the handle portion 402 adjacent circumferential groove 592 for accommodating the head portion 595 of ratchet member 582.

Figure 48:
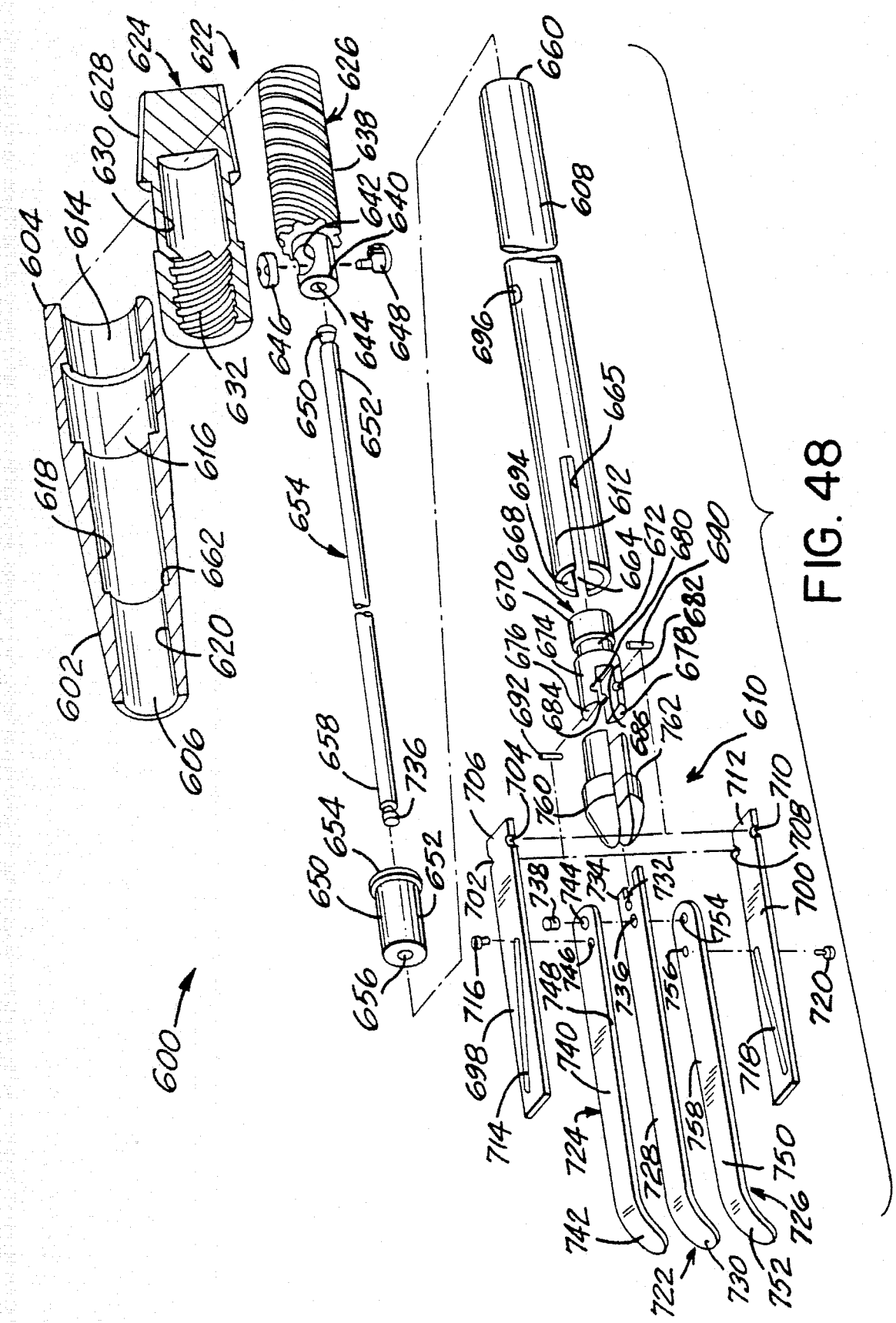
FIG. 48 is an exploded perspective view of another preferred embodiment of the surgical retractor in accordance with the subject invention.

Referring to FIG. 48, another embodiment of the surgical retractor of the subject invention is illustrated and is designated generally by reference numeral 600. Surgical retractor 600 comprises a handle portion 602 having opposed proximal and distal ends 604 and 606, an elongated endoscopic portion 608 which extends from the distal end 606 of handle portion 602, and a retractor assembly 610 operatively associated with the distal end 612 of the endoscopic portion 608.

The handle portion 602 of the surgical retractor 600 includes a stepped axial bore 614 which extends longitudinally therethrough from the proximal end 604 to the distal end 606 thereof. Axial bore 614 has a proximal chamber 616, a medial chamber 618, and a distal chamber 620 defined therein. A driving assembly 622 is associated with handle portion 602 and is mounted within the axial bore 614 for operating the retractor assembly 610. Driving assembly 622 includes a knob member 624 and a driving screw 626. Knob member 624 comprises a proximal grasping portion 628, a intermediate cavity portion 630 and a distal threaded portion 632. Knob member 624 is mountable within the axial bore 614 of handle portion 602 in such a manner so that the threaded portion 632 thereof is maintained within the proximal chamber 616 of axial bore 614. Once mounted, knob member 624 is capable of rotating with respect to the longitudinal axis of the handle portion 602. Driving screw member 626 includes a threaded body portion 638, and a distal engaging portion 640. A transverse bore 642 is formed in the distal engaging portion 640, while a longitudinal bore 642 is also formed therein. Transverse bore 642 is provided for maintaining a two-piece universal clip having a first portion 646 and a second portion 648 which are adapted and configured for maintaining and engaging a grooved tail 650 at the proximal end 652 of rod member 654.

Driving member 626 is dimensioned and configured for mounting within the knob member 624 of handle portion 602. In particular, the threaded body portion 638 of driving member 626 is engageable with the threaded bore portion 632 of knob member 624. Rotations of knob member 624 during operations of retractor 600 cause corresponding axial movements of driving member 626 relative to the longitudinal axis of the handle portion 602. The roedial chamber 618 has a diameter which is dimensioned to accommodate the axial translation of the threaded portion 638 of driving member 626 as it is driven in a distal direction within handle portion 602 in response to rotations of knob member 624.

The endoscopic portion 608 of surgical retractor 600 is mounted to the distal end 606 of handle portion 602 by a plug member 650. More particularly, plug member 650 includes a cylindrical body portion 652 and a proximal circumferential flange portion 654. An axial passageway 656 extends through the body portion 652 for permitting passage of the distal end 658 of rod member 654. To mount the endoscopic portion 608 to handle portion 602, the cylindrical body portion 652 of plug member 650 is extended into the distal end 660 of endoscopic portion 608 in such a manner so that the flange portion 654 of plug member 650 abuts the distal end 660 of endoscopic portion 608. The endoscopic portion 608 is then mountable within the distal most chamber 620 of axial bore 614 of handle portion 602 and is maintained therein by flange portion 654 of plug member 650 abutting against the wall 662 formed between medial chamber 618 and distal chamber 620. The distal end 612 of endoscopic portion 608 is provided with diametrically opposed longitudinally extending slots 664 and 665 for accommodating the retractor assembly 610.

The retractor assembly 610 of surgical retractor 600 includes a coupling member 668 which has a proximal portion 670, a roedial circumferential groove portion 672, and a slotted head portion 674 which has a pair of diametrically opposed platforms 676 and 678. An axial passage 680 extends through the coupling member 668 for permitting extension of the distal end 658 of rod member 654 therethrough. The lower platform 678 at the head portion 674 of coupling member 668 includes spaced apart notches 682 and 684, while the upper platform 676 includes spaced apart notches 686 and 688. Set pins 690 and 692 are mountable within these notches formed in the opposed platforms 676 and 678. The coupling member 668 is mountable within the axial bore 694 and is maintained therein by a crimp 696 formed in an area of the endoscopic portion 608 which becomes engaged in the circumferential groove 672 of coupling member 668 once it has been mounted therein.

Retractor assembly 610 further includes upper and lower cam beams 698 and 700. Upper cam beam 698 has a pair of spaced apart notches 702 and 704 formed in a proximal end 706 thereof, for being engaged with the set pins 692 and 690, thus rigidly maintaining cam beam 698 relative to the coupling member 668. Similarly, cam beam 700 includes a pair of spaced apart notches 708 and 710 provided adjacent the proximal end 712 there, of which are also provided for mounting with set pins 690 and 692, thus maintaining cam beam 700 in a fixed position relative to coupling member 668. A camming slot 714 is formed in upper cam beam 698 and defines a path within which a cam follower 716 translates. Camming slot 714 is disposed angularly relative to the longitudinal axis of cam beam 698. Similarly, cam beam 700 is provided with a camming slot 718 finding a path within which a cam follower 720 translates. Camming slot 718 is disposed angularly relative to the longitudinal axis of camming beam 700 and is symmetrically disposed relative to the camming slot 714 of cam beam 698. The disposition of camming slots 714 and 718 facilitates the fan-like deployment of the retractor assembly 610.

The retractor assembly 610 of surgical retractor 600 further includes a plurality of retractor blade members which includes a center retractor blade 722, an upper retractor blade 724, and a retractor lower blade 726. The center retractor blade 722 has an elongated body portion 728 and a head portion 730 which depends angularly away from the body portion 728 to define a tong structure for increasing retracting capabilities at the surgical site. A substantially I-shaped slot 732 is formed in the proximal end 734 of the center retractor blade 722. The I-shaped slot is configured and adapted for engaging a grooved head portion 736 which is formed on the distal end 658 of rod member 654. An aperture 736 is provided forwardly from the I-shaped slot 732 for mounting a pivot pin 738.

The upper retractor blade 724 includes an elongated body portion 740 and a distal head portion 742 which depends angularly away from the body portion 740. An aperture 744 is provided in body portion 740 which corresponds to the pivot pin mounting aperture 736 in the center retractor blade 722. In addition, an aperture 746 is provided in body portion 740 spaced from aperture 744 and disposed adjacent to a lateral edge 748 thereof. Aperture 746 is provided for mounting and maintaining the cam follower 716. Lower retractor blade 726 includes a body portion 750 and a distal head portion 752 which depends angularly from body portion 750 to define a tong like structure. An aperture 754 is provided in the body portion 750 which corresponds with the aperture 736 in center retractor blade 722 and the aperture 746 in upper retractor blade 724 for mounting the pivot pin 738. An additional aperture 756 is provided in the body portion 750 of lower retractor blade 726 and is disposed forward from aperture 754 and adjacent to a lateral edge 758 thereof. Aperture 756 is provided for mounting and maintaining cam follower 720. The retractor assembly 610 further includes stabilizer heads 760 and 762 which are adapted and configured for mounting within the axially passageway 694 of endoscopic portion 608 adjacent the distal end 612 thereof.

Turning now to FIGS. 49–51, in operation the retractor assembly 610 of surgical instrument 600 can be deployed from a closed position by rotating the knob member 624 in the direction of indicator arrow "C", relative to the handle portion 602. As knob member 624 is rotated, driving screw 626 is caused to translate axially relative to the handle portion 602. Thereupon, the distal engaging portion 640 of driving screw member 626 travels axially within the medial chamber 618 of handle portion 602. Accordingly, axial movement of driving screw 626 in a distal direction causes corresponding axial movements of rod member 654. Consequently, the center retractor blade 722 of retractor assembly 610 is caused to travel in a distal direction. As center blade 722 moves in a distal direction with the longitudinal axis thereof maintaining parallel relationship with the longitudinal axis of the endoscopic portion 608, the upper and lower retractor blades 724 and 726 gradually deploy outwardly with respect to the center blade 722, pivoting symmetrically about pivot pin 738 upon distal movement. The outward deployment of the upper and lower retractor blades 724 and 726 is controlled by the translation of the cam followers 716 and 720 within their corresponding camming slots 714 and 718.

The surgical retractor of the present invention is a compact, lightweight and easy to use instrument incorporating many features required during endoscopic surgical procedures which allows the surgeon to use the instrument with one hand thus freeing the other hand for manipulation of other instruments during surgery. The present retractor overcomes many of the disadvantages encountered with prior art devices and provides a precision instrument which is easy to handle and simple to manufacture.

While the invention has been particularly shown and described with reference to preferred embodiments thereof, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. A surgical retractor comprising:
   a) a handle assembly;
   b) an elongated body extending distally from the handle assembly and defining opposed proximal and distal end portions, a longitudinal axis which extends therethrough, an interior bore, and an exterior wall;
   c) a blade cavity formed within said elongated body and terminating at a location proximal of the distal end portion thereof and opening through the exterior wall of the elongated body;
   d) a retractor assembly including a plurality of interleaved blade members disposed within the blade cavity and mounted fear cooperative movement between a first position enclosed within the interior bore of the elongate body and a second position extending radially outwardly from the blade cavity through the exterior wall of the elongated body; and
   e) an actuator within the handle assembly which is movably attached to the interleaved blade members for controlled movement of said blade members out of the blade cavity.

2. A surgical retractor as recited in claim 1, wherein the blade members are cooperatively mounted to one another and supported within the elongated body by a common pivot pin.

3. A surgical retractor as recited in claim 1, wherein each of the blade members includes an angled cam slot within which a cam pin translates.

4. A surgical retractor as recited in claim 3, wherein the actuator includes an actuation shaft which extends from the handle assembly to the cam pin to effect translation thereof with respect to the angled cam slots in the blade members.

5. A surgical retractor as recited in claim 4, wherein the actuator includes an actuation member mounted for axial rotation with respect to the longitudinal axis of the elongated body.

6. A surgical retractor as recited in claim 1, wherein the retractor assembly includes first and second pairs of blade members, each pair extending through the exterior wall of the elongated body from diametrically opposed sides thereof.

7. A surgical retractor for manipulating body tissue during endoscopic surgical procedures comprising:
   a) a handle assembly;
   b) an elongated body extending distally from the handle assembly and defining a longitudinal axis;
   c) a retractor assembly disposed within an open cavity formed within said elongated body and terminating at a location proximal of the distal end portion thereof and opening through the exterior wall of the elongated body, the retractor assembly including at least three cooperating interleaved blade members mounted for movement about a common pivot axis between a closed position in alignment with one another and disposed within the open cavity, and an open position angularly disposed with respect to one another and projecting at least partially from the open cavity; and d) an actuator within the handle assembly which is movably attached to the interleaved blade members for controlled movement of said interleaved blade members out of the open cavity.

8. A surgical retractor as recited in claim 7, wherein the blade members are cooperatively mounted to one another and supported within the elongated body by a common pivot pin.

9. A surgical retractor as recited in claim 7, wherein each of the blade members includes an angled cam slot within which a cam pin translates.

10. A surgical retractor as recited in claim 9, wherein the actuator includes an actuation shaft which extends from the handle assembly to the cam pin to effect translation thereof with respect to the angled cam slots in the blade members.

11. A surgical retractor as recited in claim 10, wherein the actuator includes an actuation member mounted for axial rotation with respect to the longitudinal axis of the elongated body.

* * * * *